United States Patent [19]

Lewis et al.

[11] Patent Number: 5,756,677
[45] Date of Patent: May 26, 1998

[54] MINOR AMPULLATE SPIDER SILK PROTEINS

[75] Inventors: Randolph V. Lewis; Mark Colgin, both of Laramie, Wyo.

[73] Assignee: University of Wyoming, Laramie, Wyo.

[21] Appl. No.: 458,298

[22] Filed: Jun. 2, 1995

Related U.S. Application Data

[62] Division of Ser. No. 209,747, Mar. 14, 1994.
[51] Int. Cl.$^6$ .......................... A61K 38/17; C07K 14/435
[52] U.S. Cl. ............................................. 530/353; 530/355
[58] Field of Search ............................................ 530/353

[56] References Cited

U.S. PATENT DOCUMENTS 5,245,012   9/1993   Lombari et al. ........................ 530/353

FOREIGN PATENT DOCUMENTS 0452925   4/1991   European Pat. Off. .
452925    4/1991   European Pat. Off. .

OTHER PUBLICATIONS

Lewis, Randolph V., Acc. Chem. Res., 25 (9), pp. 392–398, 1992.
Andersen, Svend O., Comp. Biochem. Physiol., 35 (3), pp. 705–711, 1970.
Work, Robert W., Text. Res. J., 46(7), pp. 485–492, 1976.
Gosline, J. M., et al, ACS Symp. Ser., 544 (Silk Polymers), pp. 328–341, 1994.
Craig, Catherine L., ACS Symp. Ser., 544 (Silk Polymers), pp. 54–66, 1994.
Vollrath, Fritz, ACS Symp. Ser., 544 (Silk Polymers), pp. 17–28, 1994.
Kaplan, D.L., et al, Biomaterials, pp. 3–53, 1991.
Hinman, Mike, et al, Results Probl. Cell Differ., 19, pp. 227–254, 1992.
Cunniff, Philip M., et al, ACS Symp. Ser., 544, pp. 234–251, 1994.
Dong Z., et al, Arch. Biochem. Biophys. 284 (1), pp. 53–57, 1991.
Hinman, Michael B., et al, J. Biol. Chem., 267 (27), pp. 19320–19324, 1992.
Protein Polymer Technologies, Discover, pp. 32–36, Mar., 1992.
Lewis, R. V., Inside R & D, May 8, 1991.
New Scientist, p. 18, Nov. 14, 1992.
Viney, Christopher, Inside R & D, Mar. 13, 1991.
Chemical & Engineering News, pp. 26–32, Jul. 16, 1990.
New Scientist, p. 39, Sep. 29, 1998.
Chemical & Engineering News, pp. 24, 25, Jul. 25, 1988.
Department of the Army, Washington, D.C., Corp. Source Codes: 000137000, 1p., 1991.
Zemlin, J.C., Collaborative Research Inc., Waltham, Mass., Corp. Source Codes: 400817, 78p., 1968.
Gosline, John M., et al, Nature (London), 309(5968), pp. 551–552, 1984.
Dong, Z., et al, Polymer Preprints, Div. of Polym. Chem., American Chemical Society, v31 n1, pp. 197–198, 1990.
Fornes, R.E., et al, Journal of Polymer Science, Polymer Physics Ed., v21 n7, pp. 1163–1172, 1983.
Xu, M., et al, Proceedings of the National Academy of Sciences, v87, pp. 7120–7124, 1990.
Lewis, R. V., Gov. Rep. Announce. Index (U.S.), 92(4), Abstr. No. 208,659, 1992.
Dong et al. (1990) "Spider silk proteins" Polymer Preprints 31(1):197–198, Apr. 1990.

*Primary Examiner*—Robert A. Wax
*Assistant Examiner*—Kawai Lau
*Attorney, Agent, or Firm*—Birch, Stewart, Kolasch & Birch, LLP

[57] ABSTRACT cDNA clones encoding minor ampullate spidroin proteins (MiSP) are described. The translated amino acid sequence of the cloned cDNA shows that the MiSPs have a structure which exhibits an amino proximal nonrepetitive region, a repetitive portion and a carboxy-proximal nonrepetitive portion. The repetitive portion of the sequence is describable by a generic repeat formula. Comparison of the amino acid sequences derived from the translation with the sequences of short peptides obtained from solubilized minor ampullate spider silk suggests that the nonrepetitive portions of the protein are cleaved from the protein during secretion from the cells synthesizing the spidroins. This comparison also suggests that the minor ampullate spider silk is composed of at least three polypeptides.

16 Claims, 19 Drawing Sheets

```
             10          20          30          40          50
      *       *     *     *     *     *     *     *     *     *
   ACATA CTAGG TTTGG TGCCG GAGCT GGAGC TGGTA CGTCT GTGCA GAAAT 60          70          80          90         100
      *       *     *     *     *     *     *     *     *     *
   ACTTT GCACA TCACT TCTCC AATTG CTTCT CGGGT ATTTG TCAAA TGATT 110         120         130         140         150
      *       *     *     *     *     *     *     *     *     *
   AGTTC TACAA CTTCT ACTGA TCATG CAGTA AGTGT TGCTA CGAGC GTTGC 160         170         180              190
      *       *     *     *     *     *        *     *     *
   GCTGA AGTCA GCTTG GACTT GATGC AAATG CT ATG AAC AAC TTA CTA
                                          M   N   N   L   L>

200         210         220         230         240
     *     *     *     *     *     *     *     *     *     *
   GGT GCC GTT AGT GGA TAT GTT TCG ACA CTA GGC AAC GCT ATT TCT
   G   A   V   S   G   Y   V   S   T   L   G   N   A   I   S>

250         260         270         280
     *       *     *     *     *     *     *     *     *     *
   GAT GCT TCG GCA TAC GCA AAT GCT CTT TCT TCC GCT ATA GGA AAT
   D   A   S   A   Y   A   N   A   L   S   S   A   I   G   N>

290         300         310         320         330
     *     *     *     *     *     *     *     *     *     *
   GTG TTA GCT AAT TCC GGT TCA ATT AGC GAA AGC ACT GCA TCT TCT
   V   L   A   N   S   G   S   I   S   E   S   T   A   S   S>

340         350         360         370
     *       *     *     *     *     *     *     *     *     *
   GCT GCT TCC AGT GCT GCT TCT TCA GTC ACT ACA ACT TTG ACG TCT
   A   A   S   S   A   A   S   S   V   T   T   T   L   T   S>

380         390         400         410         420
     *     *     *     *     *     *     *     *     *     *
   TAT GGA CCA GCT GTA TTT TAC GCA CCT TCT GCA TCA TCT GGA GGC
   Y   G   P   A   V   F   Y   A   P   S   A   S   S   G   G>

430         440         450         460
     *       *     *     *     *     *     *     *     *     *
   TAT GGA GCT GGA GCT GGA GCT GTT GCT GCA GCA GGA GCT GCC GGC
   Y   G   A   G   A   G   A   V   A   A   A   G   A   A   G>

470         480         490         500         510
     *     *     *     *     *     *     *     *     *     *
   GCT GGA GGT TAC GGA AGA GGT GCT GGA GGC TAC GGT GGA CAA GGA
   A   G   G   Y   G   R   G   A   G   G   Y   G   G   Q   G>
```

FIG. 1A

```
     520             530             540             550
  *         *     *         *     *         *     *         *     *
GGA TAT GGT GCC GGA GCC GGA GCT GGT GCT GCT GCA GCT GCT GGA
 G   Y   G   A   G   A   G   A   G   A   A   A   A   A   G>

560             570             580             590             600
  *         *     *         *     *         *     *         *     *
GCA GGA GCC GGA GGC GCT GGT GGT TAC GGT AGA GGT GCT GGT GCT
 A   G   A   G   G   A   G   G   Y   G   R   G   A   G   A>

610             620             630             640
  *         *     *         *     *         *     *         *     *
GGA GCT GGT GCG GCT GCT GGG GCA GGT GCA GGC GCC GGT GGT GCT
 G   A   G   A   A   A   G   A   G   A   G   A   G   G   A>

650             660             670             680             690
  *         *     *         *     *         *     *         *     *
GGA TAT GGT GGA CAA GGC GGA TAT GGT GCC GGA GCA GGA GCT GGT
 G   Y   G   G   Q   G   G   Y   G   A   G   A   G   A   G>

700             710             720             730
  *         *     *         *     *         *     *         *     *
GCG GCT GCT GCT GCT GGT GCA GGA GCA GGA GGT GCT GGC GGT TAC
 A   A   A   A   A   G   A   G   A   G   G   A   G   G   Y>

740             750             760             770             780
  *         *     *         *     *         *     *         *     *
GGT AGA GGT GCT GGT GCT GGA GCA GGA GCC GCT GCG GGT GCT GGA
 G   R   G   A   G   A   G   A   G   A   A   A   G   A   G>

790             800             810             820
  *         *     *         *     *         *     *         *     *
GCT GGA GGC TAC GGT GGT CAA GGT GGG TAC GGT GCC GGA GCA GGA
 A   G   G   Y   G   G   Q   G   G   Y   G   A   G   A   G>

830             840             850             860             870
  *         *     *         *     *         *     *         *     *
GCT GGT GCG GCT GCT GCT GCT GCT GGA GCA GGA TCT GGA GGC GCT
 A   G   A   A   A   A   A   A   G   A   G   S   G   G   A>

880             890             900             910
  *         *     *         *     *         *     *         *     *
GGC GGT TAC GGT AGA GGT GCT GGT GCT GGA GCT GGA GCC GCT GCA
 G   G   Y   G   R   G   A   G   A   G   A   G   A   A   A>

920             930             940             950             960
  *         *     *         *     *         *     *         *     *
GGT GCA GGA GCA GGA GCT GGA AGC TAC GGT GGT CAA GGA TAC GGT
 G   A   G   A   G   A   G   S   Y   G   G   Q   G   Y   G>

970             980             990            1000
  *         *     *         *     *         *     *         *     *
GCC GGA GCA GGA GCT GGT GCT GCT GCA GCT GCA NNN NNN NNN NNN
 A   G   A   G   A   G   A   A   A   A   A
```

FIG. 1B

```
     1010          1020          1030          1040
  *       *      *       *     *      *      *         *
NNN  NNN  NNN  NNN  NNN  NNN  NNN  NNN  NNN  NNN  GGT  GCA  GGT  GCA
                                                   G    A    G    A>

1050          1060          1070          1080          1090
  *       *      *       *     *      *      *       *     *       *
GGT  GCT  GGA  TAT  GGT  GGA  CAA  GGC  GGA  TAT  GGT  GCC  GGA  GCA  GGA
 G    A    G    Y    G    G    Q    G    G    Y    G    A    G    A    G>

1100          1110          1120          1130
  *       *      *       *     *      *      *       *     *       *
GCT  GGT  GCG  GCT  GCT  GCT  GCT  GGT  GCA  GGA  GCT  GGA  GGT  GCT  GGT
 A    G    A    A    A    A    A    G    A    G    A    G    G    A    G>

1140          1150          1160          1170          1180
  *       *      *       *     *      *      *       *     *       *
GGT  TAC  GGT  AGA  GGT  GCT  GGT  GCT  GGA  GCT  GGA  GCC  GCT  GCA  GGT
 G    Y    G    R    G    A    G    A    G    A    G    A    A    A    G>

1190          1200          1210          1220
  *       *      *       *     *      *      *       *     *       *
GCA  GGA  GCA  GGA  GCT  GGA  GGC  TAC  GGT  GGT  CAA  AGT  GGA  TAC  GGT
 A    G    A    G    A    G    G    Y    G    G    Q    S    G    Y    G>

1230          1240          1250          1260          1270
  *       *      *       *     *      *      *       *     *       *
GCC  GGA  GCA  GGA  GCT  GCT  GCA  GCT  GCT  GGA  GCA  GGA  GCT  GGA  GGC
 A    G    A    G    A    A    A    A    A    G    A    G    A    G    G>

1280          1290          1300          1310
  *       *      *       *     *      *      *       *     *       *
GCT  GGT  GGT  TAC  GGT  GA   GGT  GCT  GGT  GCT  GGA  GCA  GGA  GCC  GCT
 A    G    G    Y    G    R    G    A    G    A    G    A    G    A    A>

1320          1330          1340          1350          1360
  *       *      *       *     *      *      *       *     *       *
GCG  GGT  GCT  GGA  GCA  GGA  GCC  GCT  GCG  GGT  GCA  GGA  GCT  GGA  GGC
 A    G    A    G    A    G    A    A    A    G    A    G    A    G    G>

1370          1380          1390          1400
  *       *      *       *     *      *      *       *     *       *
TAC  GGT  GGT  CAA  GGT  GGG  TAC  GGT  GCC  GGT  GCA  GGA  GCT  GGT  GCG
 Y    G    G    Q    G    G    Y    G    A    G    A    G    A    G    A>

1410          1420          1430          1440          1450
  *       *      *       *     *      *      *       *     *       *
GCT  GCT  GCT  GCT  GGA  GCA  GGA  GCT  GGA  GGC  GCT  GGT  GGT  TAC  GGT
 A    A    A    A    G    A    G    A    G    G    A    G    G    Y    G>

1460          1470          1480          1490
  *       *      *       *     *      *      *       *     *       *
AGA  GGT  GCT  GGT  GCT  GGA  GCT  GGA  GCT  GCT  GCA  GGC  GCA  GGA  GCT
 R    G    A    G    A    G    A    G    A    A    A    G    A    G    A>
```

FIG. 1C

```
        1500              1510              1520              1530              1540
     *         *         *         *         *         *         *         *         *
   GGA  GGC  TAC  GGT  GGT  CAA  GGT  GGA  TAC  GGT  GCC  GGA  GCA  GGA  GCT
    G    G    Y    G    G    Q    G    G    Y    G    A    G    A    G    A>

1550              1560              1570              1580
     *         *         *         *         *         *         *         *         *
   GGT  GCT  GCT  GCA  GCT  GCT  GCA  ACA  GGA  GCC  GGA  GGC  GCT  GGT  GGT
    G    A    A    A    A    A    A    T    G    A    G    G    A    G    G>

1590              1600              1610              1620              1630
     *         *         *         *         *         *         *         *         *
   TAC  GGT  AGA  GGT  GCT  GGT  GCT  GGA  GCT  GGT  GCC  GCT  GCT  GGG  GCA
    Y    G    R    G    A    G    A    G    A    G    A    A    A    G    A>

1640              1650              1660              1670
     *         *         *         *         *         *         *         *         *
   GGT  GCA  GGC  ACC  GGT  GGT  GCT  GGA  TAT  GGT  GGA  CAA  GGC  GGT  TAT
    G    A    G    T    G    G    A    G    Y    G    G    Q    G    G    Y>

1680              1690              1700              1710              1720
     *         *         *         *         *         *         *         *         *
   GGT  GCC  GGA  GCA  GGA  GCT  GGT  GCG  GCT  GCT  GCT  GCT  GGT  GCA  GGA
    G    A    G    A    G    A    G    A    A    A    A    A    G    A    G>

1730              1740              1750              1760
     *         *         *         *         *         *         *         *         *
   GCA  GGA  GGT  GCT  GGT  TAC  GGT  AGA  GGT  GCT  GGT  GCT  GGA  GCT  GGA
    A    G    G    A    G    Y    G    R    G    A    G    A    G    A    G>

1770              1780              1790              1800              1810
     *         *         *         *         *         *         *         *         *
   GCT  GCT  GCA  GGT  GCT  GGA  GCT  GGA  GCC  GCT  GCA  GGT  GCA  GGA  GCA
    A    A    A    G    A    G    A    G    A    A    A    G    A    G    A>

1820              1830              1840              1850
     *         *         *         *         *         *         *         *         *
   GGA  GCT  GGA  GGC  TAC  GGT  GGT  CAG  GGT  GGA  TAC  GGT  GCC  GGA  GCA
    G    A    G    G    Y    G    G    Q    G    G    Y    G    A    G    A>

1860              1870              1880              1890              1900
     *         *         *         *         *         *         *         *         *
   AGA  GCT  GGT  GCT  GCG  GCA  GCT  GCT  GGA  GCA  GGA  GCT  GGA  GGC  GCT
    R    A    G    A    A    A    A    A    G    A    G    A    G    G    A>

1910              1920              1930              1940
     *         *         *         *         *         *         *         *         *
   GCG  GGT  TAC  AGT  AGA  GGT  GGT  CGT  GCA  GGA  GCC  GCT  GGT  GCT  GGA
    A    G    Y    S    R    G    G    R    A    G    A    A    G    A    G>

1950              1960              1970              1980              1990
     *         *         *         *         *         *         *         *         *
   GCT  GGA  GCC  GCT  GCA  GGT  GCA  GGA  GCA  GGA  GCT  GGA  GGC  TAC  GGT
    A    G    A    A    A    G    A    G    A    G    A    G    G    Y    G>
```

FIG. 1D

```
      2000                2010                2020                2030
   *         *         *         *         *         *         *         *         *
 GGT CAA GGT GGA TAC GGT GCC GGA GCA GGA GCT GGT GCT GCT GCA
  G   Q   G   G   Y   G   A   G   A   G   A   G   A   A   A>

2040                2050                2060                2070                2080
   *         *         *         *         *         *         *         *         *
 GCT GCT GGT GCA GGA TCC GGA GGC GCT GGT GGT TAC GGT AGA GGT
  A   A   G   A   G   S   G   A   G   G   Y   G   R   G>

2090                2100                2110                2120
   *         *         *         *         *         *         *         *         *
 GCT GGT GCT GGA GCC GCT GCA GGA GCT GGA GCC GCT GCA GGT GCT
  A   G   A   G   A   A   A   G   A   G   A   A   A   G   A>

2130                2140                2150                2160                2170
   *         *         *         *         *         *         *         *         *
 GGA GCA GGA GCT GGA GGC TAC GGT GGT CAA GGT GGA TAC GGT GCC
  G   A   G   A   G   G   Y   G   G   Q   G   G   Y   G   A>

2180                2190                2200                2210
   *         *         *         *         *         *         *         *         *
 GGA GCA GGA GCT GCT GCA GCT GCT GGA GCA GGA GCC GGA CGT GGA
  G   A   G   A   A   A   A   A   G   A   G   A   G   R   G>

2220                2230                2240                2250                2260
   *         *         *         *         *         *         *         *         *
 GGT TAC GGA AGA GGT GCT GGT GCT GGA GGC TAC GGT GGA CAA GGA
  G   Y   G   R   G   A   G   A   G   G   Y   G   G   Q   G>

2270                2280                2290                2300
   *         *         *         *         *         *         *         *         *
 GGA TAT GGT GCC GGA GCT GGA GCC GGT GCT GCT GCA GCT GCT GGA
  G   Y   G   A   G   A   G   A   G   A   A   A   A   A   G>

2310                2320                2330                2340                2350
   *         *         *         *         *         *         *         *         *
 GCG GGA GCC GGA GGC TAT GGC GAC AAG GAG ATA GCC TGC TGG AGC
  A   G   A   G   G   Y   G   D   K   E   I   A   C   W   S>

2360                2370                2380                2390
   *         *         *         *         *         *         *         *         *
 AGG TGT AGA TAC ACT GTT GCC TCC ACA ACA TCT CGT TTG AGT TCG
  R   C   R   Y   T   V   A   S   T   T   S   R   L   S   S>

2400                2410                2420                2430                2440
   *         *         *         *         *         *         *         *         *
 GCC GAA GCA TCT TCT AGG ATA TCG TCG GCG GCT TCC ACT TTA GTA
  A   E   A   S   S   R   I   S   S   A   A   S   T   L   V>

2450                2460                2470                2480
   *         *         *         *         *         *         *         *         *
 TCT GGA GGT TAC TTG AAT ACA GCA GCT CTG CCA TCG GTT ATT TCG
  S   G   G   Y   L   N   T   A   A   L   P   S   V   I   S>
```

FIG. 1E

```
       2490              2500             2510             2520             2530
  *       *       *       *       *       *       *       *       *       *
  GAT     CTT     TTT     GCC     CAA     GTT     GGT     GCA     TCT     TCT     CCG     GTG     ATC     AGA     CAG
  D       L       F       A       Q       V       G       A       S       S       P       V       I       R       Q>

2540             2550             2560             2570
      *       *       *       *       *       *       *       *       *
      CGA     AGT     TTG     ATC     CAA     GTT     TTG     TTG     GAA     ATT     GTT     TCT     TCT     CTT     ATC
      R       S       L       I       Q       V       L       L       E       I       V       S       S       L       I>

2580             2590             2600             2610             2620
  *       *       *       *       *       *       *       *       *       *
  CAT     ATT     CTC     AGT     TCT     TCT     AGC     GTA     GGA     CAA     GTC     GAT     TTC     AGT     TCG
  H       I       L       S       S       S       S       V       G       Q       V       D       F       S       S>

2630             2640             2650             2660
      *       *       *       *       *       *       *       *       *
      GTT     GGG     TCG     TCT     GCT     GCA     GCT     GTT     GGT     CAA     TCC     ATG     CAA     GTT     GTA
      V       G       S       S       A       A       A       V       G       Q       S       M       Q       V       V>

2670             2680             2690             2700             2710
  *       *       *       *       *       *       *       *       *       *
  ATG     GGC     TAA     ACAT    GATGG   TTCTC   TCAAT   TATGT   ATTCT   TTAAT   TACCG
  M       G       *>

2720             2730             2740             2750             2760
  *       *       *       *       *       *       *       *       *       *
  CTAAG   GTAGC   AAAAT   ATTGT   AAAGT   AAAGT   TTTCT   TACAA   AATAA   AAATT 2770             2780             2790
  *       *       *       *       *
  CTTTT   CTGCA   AAAAA   AAAAA   AAAAA   AA
```

FIG. 1F

```
            10              20              30              40
             *       *       *       *       *       *       *       *       *
TCT TAT GGA CCA TCC GTA TTT TAC ACT CCT ACT TCA GCT GGA AGC
 S   Y   G   P   S   V   F   Y   T   P   T   S   A   G   S>

50              60              70              80              90
             *       *       *       *       *       *       *       *       *
TAT GGT GCA GGG GCC GGA GGT TTT GGA GCT GGA GCC TCT GCT GGT
 Y   G   A   G   A   G   F   G   A   G   A   S   A   G>

100             110             120             130
     *       *       *       *       *       *       *       *       *
GTC GGA GCC GGA GCT GGT ACT GTA GCA GGA TAT GGT GGA CAA GGA
 V   G   A   G   A   G   T   V   A   G   Y   G   G   Q   G>

140             150             160             170             180
     *       *       *       *       *       *       *       *       *
GGA TAT GGT GCC GGA AGC GCT GGA GGT TAT GGA AGA GGT ACT GGA
 G   Y   G   A   G   S   A   G   G   Y   G   R   G   T   G>

190             200             210             220
     *       *       *       *       *       *       *       *       *
GCT GGA GCC GCT GCT GGT GCC GGA GCA GGA GCC ACT GCT GGT GCC
 A   G   A   A   G   A   G   A   G   A   T   A   G   A>

230             240             250             260             270
     *       *       *       *       *       *       *       *       *
GGA GCA GGA GCC GCT GCT GGT GCC GGA GCA GGA GCA GGT AAT TCA
 G   A   G   A   A   A   G   A   G   A   G   A   G   N   S>

280             290             300
     *       *       *       *       *       *       *
GGA GGA TAT AGT GCC GGA GTA GGA GTT GGT GCT GCA GCT
 G   G   Y   S   A   G   V   G   V   G   A   A   A>
```

FIG. 2A

```
                10                  20                  30                  40
       *         *         *         *         *         *         *         *
    CT GCA GCT GCT GGA GGA GGT GCC GGA ACT GTT GGA GGT TAC GGA
       A   A   A   G   G   G   A   G   T   V   G   G   Y   G>

50                  60                  70                  80
  *      *         *         *         *         *         *         *
 AGA GGT GCT GGT GTA GGA GCA GGT GCC GCT GCT GGT TTT GCG GCA
  R   G   A   G   V   G   A   G   A   A   G   F   A   A>

90            100           110           120           130
  *     *       *      *       *      *      *      *       *
 GGA GCT GGT GGT GCT GGA GGC TAC AGA AGA GAT GGA GGA TAC GGT
  G   A   G   G   A   G   G   Y   R   R   D   G   G   Y   G>

140           150           160
    *       *      *      *      *      *      *
 GCT GGA GCA GGA GCT GGA GCT GCT GCA GCT G
  A   G   A   G   A   G   A   A   A   X>
```

FIG. 2B

```
         10              20              30              40
          *       *       *       *       *       *       *       *       *
GGT GCA GGA GCC TAT GGA AGA GGT GCT GGA GCT GGA GCT GCT GCA
 G   A   G   G   Y   G   R   G   A   G   A   G   A   A   A>

50              60              70              80              90
          *       *       *       *       *       *       *       *       *
GTC GCA GGT GCA GAT GCT GGT GGC TAT GGA AGA AAT TAT GGT GCT
 V   A   G   A   D   A   G   G   Y   G   R   N   Y   G   A>

100             110             120             130
          *       *       *       *       *       *       *       *       *
GGA ACC ACT GCT TAT GCA GGA GCC AGA GCC GGT GGT GCT GGA GGC
 G   T   T   A   Y   A   G   A   R   A   G   G   A   G   G>

140             150             160             170             180
          *       *       *       *       *       *       *       *       *
TAT GGC GGA CAA GGA GGA TAT TCT TCT GGA GCC GGT GCT GCT GCA
 Y   G   G   Q   G   G   Y   S   S   G   A   G   A   A   A>

190             200             210             220
          *       *       *       *       *       *       *       *       *
GCT TCT GGA GCA GGA GCC GAT ATC ACT AGT GGA TAC GGA AGA GGT
 A   S   G   A   G   A   D   I   T   S   G   Y   G   R   G>

230             240             250             260             270
          *       *       *       *       *       *       *       *       *
GTT GGT GCT GGA GCT GGA GCA GAA ACT ATA GGT GCT GGA GGC TAT
 V   G   A   G   A   G   A   E   T   I   G   A   G   G   Y>

280             290             300             310
          *       *       *       *       *       *       *       *       *
GGA GGT GGG GCT GGA TCA GGA GCA CGT GCG GCT TCA GCA TCC GGA
 G   G   G   A   G   S   G   A   R   A   A   S   A   S   G>

320             330             340             350             360
          *       *       *       *       *       *       *       *       *
GCT GGT ACT GGA TAT GGT TCG TCT GGA GGT TAT AAC GTA GGT ACC
 A   G   T   G   Y   G   S   S   G   G   Y   N   V   G   T>

370             380             390             400
          *       *       *       *       *       *       *       *       *
GGA ATA AGT ACT TCT TCT GGC GCT GCA TCT AGC TAC TCT GTT TCT
 G   I   S   T   S   S   G   A   A   S   S   Y   S   V   S>

410             420             430             440             450
          *       *       *       *       *       *       *       *       *
GCT GGA GGT TAT GCT TCA ACA GGT GTT GGT ATT GGA TCC ACT GTT
 A   G   G   Y   A   S   T   G   V   G   I   G   S   T   V>

460             470             480             490
          *       *       *       *       *       *       *       *       *
ACA TCC ACA ACA TCT CGT TTG AGT TCT GCT GAA GCA TGT TCT AGA
 T   S   T   T   S   R   L   S   S   A   E   A   C   S   R>
```

FIG. 2C

```
      500             510             520             530             540
       *       *       *       *       *       *       *       *       *
      ATA     TCT     GCT     GCG     GCT     TCC     ACT     TTA     GTA     TCT     GGA     TCC     TTG     AAT     ACT
       I       S       A       A       A       S       T       L       V       S       G       S       L       N       T>

550             560             570             580
               *       *       *       *       *       *       *       *       *
      GCA     GCT     TTA     CCA     TCT     GTA     ATT     TCG     GAT     CTT     TTT     GCC     CAA     GTT     AGT
       A       A       L       P       S       V       I       S       D       L       F       A       Q       V       S>

590             600             610             620             630
               *       *       *       *       *       *       *       *       *
      GCA     TCA     TCA     CCC     GGG     GTA     TCA     GGT     AAC     GAA     GTT     TTG     ATT     CAA     GTT
       A       S       S       P       G       V       S       G       N       E       V       L       I       Q       V>

640             650             660             670
               *       *       *       *       *       *       *       *       *
      TTG     TTG     GAA     ATT     GTT     TCT     TCT     CTT     ATC     CAT     ATT     CTT     AGT     TCT     TCT
       L       L       E       I       V       S       S       L       I       H       I       L       S       S       S>

680             690             700             710             720
               *       *       *       *       *       *       *       *       *
      AGT     GTA     GGG     CAA     GTA     GAT     TTC     AGT     TCT     GTT     GGT     TCA     TCT     GCT     GCA
       S       V       G       Q       V       D       F       S       S       V       G       S       S       A       A>

730             740             750             760
               *       *       *       *       *       *       *       *       *
      GCC     GTT     GGT     CAA     TCC     ATG     CAA     GTT     GTA     ATG     GGT     TAA     AACA    AAATG
       A       V       G       Q       S       M       Q       V       V       M       G       *>

770             780             790             800             810
               *       *       *       *       *       *       *       *       *       *
             GCTCT   CTCTC   TGTTA   TATGC   ATTCT   GTAAT   TTCTT   CTAAA   CTATT   AAAAT 820             830             840             850             860
               *       *       *       *       *       *       *       *       *       *
             AATGT   AATAA   TTTCC   TGCAT   AAATA   AAAAT   ATTTT   TCTGC   AAAAA   AAAAA

870
               *
             AAAAA
```

FIG. 2D

```
              10           20           30           40
      *        *    *       *    *       *    *       *    *
GCT  GGA  GCT  GCT  GCT  GGT  GCT  GGA  GGC  TAT  GAC  GGA  CAA  GGA  GGA  TAT
 A    G    A    A    A    G    A    G    G    Y    D    G    Q    G    G    Y>

50           60           70           80           90
  *    *       *    *       *    *       *    *       *    *
GGT  GCT  GGA  GCA  GGA  GCT  GCT  GCA  GCT  GCT  GGA  GCA  GGA  GCC  GGA  AGC
 G    A    G    A    G    A    A    A    A    A    G    A    G    A    G    S>

100          110          120          130          140
  *    *       *    *       *    *       *    *       *    *
GTT  GGA  GGT  TAT  GGA  ACA  GGT  GCT  GTA  GCT  GGA  TCT  GGA  ACA  GCT  GCT
 V    G    G    Y    G    T    G    A    V    A    G    S    G    T    A    A>

150          160
  *    *       *    *       *
GGT  GCA  GGA  GCC  AGA  GCT  GGT
 G    A    G    A    R    A    G>
```

FIG. 3A

```
              10              20              30              40
    *        *        *        *        *        *        *        *
GGA GCT GCT GCT GGT GCA GGA GCC GGA GCA GGT AGT ACA GGA GGC TTT
 G   A   A   A   G   A   G   A   G   A   G   S   T   G   G   F>

50              60              70              80              90
  *        *        *        *        *        *        *        *        *        *
GGC GGA CAA GGA GGA TAT GGT GCC GGT GCA GGA GCT GCA GCT GCT GGA
 G   G   Q   G   G   Y   G   A   G   A   G   A   A   A   A   G>

100             110             120             130             140
     *        *        *        *        *        *        *        *        *
GCT TTT GCC GGA AGA GCT GGG GGT TAC GGA AGA GCT GCT GGA GCT GCG
 A   F   A   G   R   A   G   G   Y   G   R   A   A   G   A   A>

150             160             170             180             190
  *        *        *        *        *        *        *        *        *        *
GCT GGA ACT GGA GCT GCT GCT GGT GCA GGA GCC GGA GCT GGT AGT ACA
 A   G   T   G   A   A   A   G   A   G   A   G   A   G   S   T>

200             210             220             230             240
  *        *        *        *        *        *        *        *        *        *
GGA GGC TTT GGC GGA CAA AGA GGA TAC GGT GCC GGC AGA AGT AAT GGA
 G   G   F   G   G   Q   R   G   Y   G   A   G   R   S   N   G>
```

FIG. 3B

```
            10          20          30          40
    *        *    *      *      *    *      *    *    *
TAT GGT GGA CAA GGC GGA TAT GGT GCT GGA GCA GGA GCT GGT GCT GCT
 Y   G   G   Q   G   G   Y   G   A   G   A   G   A   G   A   A>

50          60          70          80          90
 *        *    *      *      *    *      *      *    *      *
GCA GCC GCA GGA TAT GGA GCC GGT GCT GGA GGA TAC GGT GGA CAA GCT
 A   A   A   G   Y   G   A   G   A   G   G   Y   G   G   Q   A>

100         110         120         130         140
    *        *    *      *      *    *      *      *    *    *
GGT TAT GGT GCC GGA GCT GGA GCT GGT AGT TCT GCA GGA AAT GCT TTC
 G   Y   G   A   G   A   G   A   G   S   S   A   G   N   A   F>
```

FIG. 3C

```
N-TERMINI: MiSp1 vs. MiSp2

MiSp1:  M N N L L F A V S G Y V S T L G N A I S D A S A Y A N A L S S A I G N V L A N S G S I S E S T A S S A A S S
MiSp2:

MiSp1:  A A S S V T T T L T S Y G P A V F Y A P S A S S G G Y G A G A A A G A G A V A A A G A G A A G G Y G R G A G G Y G G
MiSp2:          ... S Y G P S V F Y T P - T S A G S Y G A G A F G A G A S A G V G A G A G T V A G Y G G

MiSp1:  Q G G Y G A G A G A A A A G A G A G A G G A G G Y G A G A G A A A G A G A G A G G A ...
MiSp2:  Q G G Y G A G A G S A G G Y G R G T G A G A G A A A G A G A G A T A G A G A A A G A G A G ...

C-TERMINI: MiSp1 vs. MiSp2

MiSp1:  D K E I A C W S R C R Y T V A S T T T S R L S S A E A A S S R H S S A A S T L V S G G Y L N T A A A L P S V I S D
MiSp2:  G G Y A S T G V G I G S T V T S T F S R L S S A E A C S R I S A A A A S T L V S G G S L N T A A L P S V I S D

MiSp1:  L F A Q V G A S S P - V I R Q R S L I H Q V L E I H V S S L I H I L S S S S V G K V D F S S V G S S A A A V G
MiSp2:  L F A Q V S A S S P G V S G N E V L I H Q V L L E I H V S S L I H I L S S S S V G Q V D F S S V G S S A A A V G

MiSp1:  Q S M Q V V M G stop
MiSp2:  Q S M Q V V V M G stop
```

FIG. 4

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
( A ) LENGTH: 2793 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( v i ) ORIGINAL SOURCE:
( A ) ORGANISM: Nephila clavipes
( F ) TISSUE TYPE: minor ampullate gland ( i x ) FEATURE:
( A ) NAME/KEY: CDS
( B ) LOCATION: 183..2675
( D ) OTHER INFORMATION: /product="N. clavipes minor ampullate silk protein"

( x i ) SEQUENCE DESCRIPTION: SEQ ID NO:1:

| | | | | | | |
|---|---|---|---|---|---|---|
| ACATACTAGG | TTTGGTGCCG | GAGCTGGAGC | TGGTACGTCT | GTGCAGAAAT | ACTTTGCACA | 60 |
| TCACTTCTCC | AATTGCTTCT | CGGGTATTTG | TCAAATGATT | AGTTCTACAA | CTTCTACTGA | 120 |
| TCATGCAGTA | AGTGTTGCTA | CGAGCGTTGC | GCTGAAGTCA | GCTTGGACTT | GATGCAAATG | 180 |
| CTATGAACAA | CTTACTAGGT | GCCGTTAGTG | GATATGTTTC | GACACTAGGC | AACGCTATTT | 240 |
| CTGATGCTTC | GGCATACGCA | AATGCTCTTT | CTTCCGCTAT | AGGAAATGTG | TTAGCTAATT | 300 |
| CCGGTTCAAT | TAGCGAAAGC | ACTGCATCTT | CTGCTGCTTC | CAGTGCTGCT | TCTTCAGTCA | 360 |
| CTACAACTTT | GACGTCTTAT | GGACCAGCTG | TATTTTACGC | ACCTTCTGCA | TCATCTGGAG | 420 |
| GCTATGGAGC | TGGAGCTGGA | GCTGTTGCTG | CAGCAGGAGC | TGCCGGCGCT | GGAGGTTACG | 480 |
| GAAGAGGTGC | TGGAGGCTAC | GGTGGACAAG | GAGGATATGG | TGCCGGAGCC | GGAGCTGGTG | 540 |
| CTGCTGCAGC | TGCTGGAGCA | GGAGCCGGAG | GCGCTGGTGG | TTACGGTAGA | GGTGCTGGTG | 600 |
| CTGGAGCTGG | TGCGGCTGCT | GGGGCAGGTG | CAGGCGCCGG | TGGTGCTGGA | TATGGTGGAC | 660 |
| AAGGCGGATA | TGGTGCCGGA | GCAGGAGCTG | GTGCGGCTGC | TGCTGCTGGT | GCAGGAGCAG | 720 |
| GAGGTGCTGG | CGGTTACGGT | AGAGGTGCTG | GTGCTGGAGC | AGGAGCCGCT | GCGGGTGCTG | 780 |
| GAGCTGGAGG | CTACGGTGGT | CAAGGTGGGT | ACGGTGCCGG | AGCAGGAGCT | GGTGCGGCTG | 840 |
| CTGCTGCTGC | TGGAGCAGGA | TCTGGAGGCG | CTGGCGGTTA | CGGTAGAGGT | GCTGGTGCTG | 900 |
| GAGCTGGAGC | CGCTGCAGGT | GCAGGAGCAG | GAGCTGGAAG | CTACGGTGGT | CAAGGATACG | 960 |
| GTGCCGGAGC | AGGAGCTGGT | GCTGCTGCAG | CTGCANNNNN | NNNNNNNNNN | NNNNNNNNNN | 1020 |

```
NNNNNNNNNN NNNNNNNGGT GCAGGTGCAG GTGCTGGATA TGGTGGACAA GGCGGATATG      1080
GTGCCGGAGC AGGAGCTGGT GCGGCTGCTG CTGCTGGTGC AGGAGCTGGA GGTGCTGGTG      1140
GTTACGGTAG AGGTGCTGGT GCTGGAGCTG GAGCCGCTGC AGGTGCAGGA GCAGGAGCTG      1200
GAGGCTACGG TGGTCAAAGT GGATACGGTG CCGGAGCAGG AGCTGCTGCA GCTGCTGGAG      1260
CAGGAGCTGG AGGCGCTGGT GGTTACGGTG AGGTGCTGGT GCTGGAGCAG GAGCCGCTGC      1320
GGGTGCTGGA GCAGGAGCCG CTGCGGGTGC AGGAGCTGGA GGCTACGGTG GTCAAGGTGG      1380
GTACGGTGCC GGTGCAGGAG CTGGTGCGGC TGCTGCTGCT GGAGCAGGAG CTGGAGGCGC      1440
TGGTGGTTAC GGTAGAGGTG CTGGTGCTGG AGCTGGAGCT GCTGCAGGCG CAGGAGCTGG      1500
AGGCTACGGT GGTCAAGGTG GATACGGTGC CGGAGCAGGA GCTGGTGCTG CTGCAGCTGC      1560
TGCAACAGGA GCCGGAGGCG CTGGTGGTTA CGGTAGAGGT GCTGGTGCTG GAGCTGGTGC      1620
CGCTGCTGGG GCAGGTGCAG GCACCGGTGG TGCTGGATAT GGTGGACAAG GCGGTTATGG      1680
TGCCGGAGCA GGAGCTGGTG CGGCTGCTGC TGCTGGTGCA GGAGCAGGAG GTGCTGGTTA      1740
CGGTAGAGGT GCTGGTGCTG GAGCTGGAGC TGCTGCAGGT GCTGGAGCTG GAGCCGCTGC      1800
AGGTGCAGGA GCAGGAGCTG GAGGCTACGG TGGTCAGGGT GGATACGGTG CCGGAGCAAG      1860
AGCTGGTGCT GCGGCAGCTG CTGGAGCAGG AGCTGGAGGC GCTGCGGGTT ACAGTAGAGG      1920
TGGTCGTGCA GGAGCCGCTG GTGCTGGAGC TGGAGCCGCT GCAGGTGCAG GAGCAGGAGC      1980
TGGAGGCTAC GGTGGTCAAG GTGGATACGG TGCCGGAGCA GGAGCTGGTG CTGCTGCAGC      2040
TGCTGGTGCA GGATCCGGAG GCGCTGGTGG TTACGGTAGA GGTGCTGGTG CTGGAGCCGC      2100
TGCAGGAGCT GGAGCCGCTG CAGGTGCTGG AGCAGGAGCT GGAGGCTACG GTGGTCAAGG      2160
TGGATACGGT GCCGGAGCAG GAGCTGCTGC AGCTGCTGGA GCAGGAGCCG GACGTGGAGG      2220
TTACGGAAGA GGTGCTGGTG CTGGAGGCTA CGGTGGACAA GGAGGATATG GTGCCGGAGC      2280
TGGAGCCGGT GCTGCTGCAG CTGCTGGAGC GGGAGCCGGA GGCTATGGCG ACAAGGAGAT      2340
AGCCTGCTGG AGCAGGTGTA GATACACTGT TGCCTCCACA ACATCTCGTT TGAGTTCGGC      2400
CGAAGCATCT TCTAGGATAT CGTCGGCGGC TTCCACTTTA GTATCTGGAG GTTACTTGAA      2460
TACAGCAGCT CTGCCATCGG TTATTTCGGA TCTTTTTGCC CAAGTTGGTG CATCTTCTCC      2520
GGTGATCAGA CAGCGAAGTT TGATCCAAGT TTTGTTGGAA ATTGTTTCTT CTCTTATCCA      2580
TATTCTCAGT TCTTCTAGCG TAGGACAAGT CGATTTCAGT TCGGTTGGGT CGTCTGCTGC      2640
AGCTGTTGGT CAATCCATGC AAGTTGTAAT GGGCTAAACA TGATGGTTCT CTCAATTATG      2700
TATTCTTTAA TTACCGCTAA GGTAGCAAAA TATTGTAAAG TAAAGTTTTC TTACAAAATA      2760
AAAATTCTTT TCTGCAAAAA AAAAAAAAAA AAA                                   2793
```

( 2 ) INFORMATION FOR SEQ ID NO:2:

( i ) SEQUENCE CHARACTERISTICS:
        ( A ) LENGTH: 832 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: N. clavipes
        ( F ) TISSUE TYPE: minor ampullate gland ( i x ) FEATURE:
 ( A ) NAME/KEY: CDS
 ( B ) LOCATION: 1..309

( x i ) SEQUENCE DESCRIPTION: SEQ ID NO:2:

| Met 1 | Asn | Asn | Leu | Leu 5 | Gly | Ala | Val | Ser | Gly 10 | Tyr | Val | Ser | Thr | Leu 15 | Gly |
|---|---|---|---|---|---|---|---|---|---|---|---|---|---|---|---|
| Asn | Ala | Ile | Ser 20 | Asp | Ala | Ser | Ala | Tyr 25 | Ala | Asn | Ala | Leu | Ser 30 | Ser | Ala |
| Ile | Gly | Asn 35 | Val | Leu | Ala | Asn | Ser 40 | Gly | Ser | Ile | Ser | Glu 45 | Ser | Thr | Ala |
| Ser | Ser 50 | Ala | Ala | Ser | Ser | Ala 55 | Ala | Ser | Ser | Val | Thr 60 | Thr | Thr | Leu | Thr |
| Ser 65 | Tyr | Gly | Pro | Ala | Val 70 | Phe | Tyr | Ala | Pro | Ser 75 | Ala | Ser | Ser | Gly | Gly 80 |
| Tyr | Gly | Ala | Gly | Ala 85 | Gly | Ala | Val | Ala | Ala 90 | Ala | Gly | Ala | Ala 95 | Gly | Ala |
| Gly | Gly | Tyr | Gly 100 | Arg | Gly | Ala | Gly | Gly 105 | Tyr | Gly | Gly | Gln | Gly 110 | Gly | Tyr |
| Gly | Ala | Gly 115 | Ala | Gly | Ala | Gly | Ala 120 | Ala | Ala | Ala | Ala | Gly 125 | Ala | Gly | Ala |
| Gly | Gly | Ala 130 | Gly | Gly | Tyr | Gly 135 | Arg | Gly | Ala | Gly | Ala 140 | Gly | Ala | Gly | Ala |
| Ala 145 | Ala | Gly | Ala | Gly | Ala 150 | Gly | Ala | Gly | Gly | Ala 155 | Gly | Tyr | Gly | Gly | Gln 160 |
| Gly | Gly | Tyr | Gly | Ala 165 | Gly | Ala | Gly | Ala | Gly 170 | Ala | Ala | Ala | Ala | Ala 175 | Gly |
| Ala | Gly | Ala | Gly 180 | Gly | Ala | Gly | Gly | Tyr 185 | Gly | Arg | Gly | Ala | Gly 190 | Ala | Gly |
| Ala | Gly | Ala 195 | Ala | Ala | Gly | Ala | Gly 200 | Ala | Gly | Gly | Tyr | Gly 205 | Gly | Gln | Gly |
| Gly | Tyr 210 | Gly | Ala | Gly | Ala 215 | Gly | Ala | Gly | Ala | Ala 220 | Ala | Ala | Ala | Ala | Gly |
| Ala 225 | Gly | Ser | Gly | Gly | Ala 230 | Gly | Gly | Tyr | Gly | Arg 235 | Gly | Ala | Gly | Ala | Gly 240 |
| Ala | Gly | Ala | Ala | Ala 245 | Gly | Ala | Gly | Ala | Gly 250 | Ala | Gly | Ser | Tyr | Gly 255 | Gly |
| Gln | Gly | Tyr | Gly 260 | Ala | Gly | Ala | Gly 265 | Ala | Gly | Ala | Ala | Ala 270 | Ala | Ala | Xaa |
| Xaa | Xaa | Xaa 275 | Xaa | Xaa | Xaa | Xaa | Xaa 280 | Xaa | Xaa | Xaa | Xaa | Xaa 285 | Xaa | Gly | Ala |
| Gly | Ala 290 | Gly | Ala | Gly | Tyr | Gly 295 | Gly | Gln | Gly | Gly | Tyr 300 | Gly | Ala | Gly | Ala |
| Gly 305 | Ala | Gly | Ala | Ala 310 | Ala | Ala | Ala | Gly | Ala 315 | Gly | Ala | Gly | Gly | Ala 320 |
| Gly | Tyr | Gly | Arg | Gly 325 | Ala | Gly | Ala | Gly | Ala 330 | Gly | Ala | Ala | Ala | Gly 335 | Ala |
| Gly | Ala | Gly | Ala 340 | Gly | Gly | Tyr | Gly | Gly 345 | Gln | Ser | Gly | Tyr | Gly 350 | Ala | Gly |
| Ala | Gly 355 | Ala | Ala | Ala | Ala | Ala 360 | Gly | Ala | Gly | Ala | Gly 365 | Gly | Ala | Gly | Gly |
| Tyr | Gly 370 | Arg | Gly | Ala | Gly 375 | Gly | Ala | Gly | Ala 380 | Ala | Ala | Gly | Ala | Gly |
| Ala 385 | Gly | Ala | Ala | Ala 390 | Gly | Ala | Gly | Ala | Gly 395 | Gly | Tyr | Gly | Gly | Gln | Gly 400 |

| | | | | | | | | | | | | | | |
|---|---|---|---|---|---|---|---|---|---|---|---|---|---|---|
Gly|Tyr|Gly|Ala|Gly|Ala|Gly|Ala|Gly|Ala|Ala|Ala|Ala|Ala|Gly|Ala
| | | |405| | | |410| | | | |415| |
Gly|Ala|Gly|Gly|Ala|Gly|Gly|Tyr|Gly|Arg|Gly|Ala|Gly|Ala|Gly|Ala
| | | |420| | | |425| | | | |430| |
Gly|Ala|Ala|Ala|Gly|Ala|Gly|Ala|Gly|Gly|Tyr|Gly|Gly|Gln|Gly|Gly
| | |435| | | |440| | | | |445| | |
Tyr|Gly|Ala|Gly|Ala|Gly|Ala|Gly|Ala|Ala|Ala|Ala|Ala|Ala|Thr|Gly
| |450| | | |455| | | | |460| | | |
Ala|Gly|Gly|Ala|Gly|Gly|Tyr|Gly|Arg|Gly|Ala|Gly|Ala|Gly|Ala|Gly
465| | | |470| | | |475| | | | | |480|
Ala|Ala|Ala|Gly|Ala|Gly|Ala|Gly|Thr|Gly|Gly|Ala|Gly|Tyr|Gly|Gly
| | | |485| | | |490| | | | |495| |
Gln|Gly|Gly|Tyr|Gly|Ala|Gly|Ala|Gly|Ala|Gly|Ala|Ala|Ala|Ala|Ala
| | | |500| | | |505| | | | |510| |
Gly|Ala|Gly|Ala|Gly|Gly|Ala|Gly|Tyr|Gly|Arg|Gly|Ala|Gly|Ala|Gly
| | | |515| | | |520| | | | |525| |
Ala|Gly|Ala|Ala|Ala|Gly|Ala|Gly|Ala|Gly|Ala|Ala|Ala|Gly|Ala|Gly
| | |530| | | |535| | | | |540| | |
Ala|Gly|Ala|Gly|Gly|Tyr|Gly|Gly|Gln|Gly|Gly|Tyr|Gly|Ala|Gly|Ala
545| | | |550| | | |555| | | | | |560|
Arg|Ala|Gly|Ala|Ala|Ala|Ala|Ala|Gly|Ala|Gly|Ala|Gly|Gly|Ala|Ala
| | | |565| | | |570| | | | |575| |
Gly|Tyr|Ser|Arg|Gly|Gly|Arg|Ala|Gly|Ala|Gly|Ala|Gly|Ala|Gly|Ala
| | |580| | | |585| | | | |590| | |
Ala|Ala|Ala|Gly|Ala|Gly|Ala|Gly|Ala|Gly|Gly|Tyr|Gly|Gly|Gln|Gly
| |595| | | |600| | | | |605| | | |
Gly|Tyr|Gly|Ala|Gly|Ala|Gly|Ala|Gly|Ala|Ala|Ala|Ala|Ala|Gly|Ala
| |610| | | |615| | | | |620| | | |
Gly|Ser|Gly|Gly|Ala|Gly|Gly|Tyr|Gly|Arg|Gly|Ala|Gly|Ala|Gly|Ala
625| | | |630| | | |635| | | | | |640|
Ala|Ala|Gly|Ala|Gly|Ala|Ala|Ala|Gly|Ala|Gly|Ala|Gly|Ala|Gly|Gly
| | | |645| | | |650| | | | |655| |
Tyr|Gly|Gly|Gln|Gly|Gly|Tyr|Gly|Ala|Gly|Ala|Gly|Ala|Ala|Ala|Ala
| | |660| | | |665| | | | |670| | |
Ala|Gly|Ala|Gly|Ala|Gly|Arg|Gly|Gly|Tyr|Gly|Arg|Gly|Ala|Gly|Ala
| | |675| | | |680| | | | |685| | |
Gly|Gly|Tyr|Gly|Gly|Gln|Gly|Gly|Tyr|Gly|Ala|Gly|Ala|Gly|Ala|Gly
| |690| | | |695| | | | |700| | | |
Ala|Ala|Ala|Ala|Ala|Gly|Ala|Gly|Ala|Gly|Gly|Tyr|Gly|Asp|Lys|Glu
705| | | | |710| | | |715| | | | | |720
Ile|Ala|Cys|Trp|Ser|Arg|Cys|Arg|Tyr|Thr|Val|Ala|Ser|Thr|Thr|Ser
| | | |725| | | |730| | | | |735| |
Arg|Leu|Ser|Ser|Ala|Glu|Ala|Ser|Ser|Arg|Ile|Ser|Ser|Ala|Ala|Ser
| | |740| | | |745| | | | |750| | |
Thr|Leu|Val|Ser|Gly|Gly|Tyr|Leu|Asn|Thr|Ala|Ala|Leu|Pro|Ser|Val
| |755| | | |760| | | | |765| | | |
Ile|Ser|Asp|Leu|Phe|Ala|Gln|Val|Gly|Ala|Ser|Ser|Pro|Val|Ile|Arg
|770| | | | |775| | | | |780| | | |
Gln|Arg|Ser|Leu|Ile|Gln|Val|Leu|Leu|Glu|Ile|Val|Ser|Ser|Leu|Ile
785| | | | |790| | | |795| | | | | |800
His|Ile|Leu|Ser|Ser|Ser|Ser|Val|Gly|Gln|Val|Asp|Phe|Ser|Ser|Val
| | | |805| | | |810| | | | |815| |
Gly|Ser|Ser|Ala|Ala|Ala|Val|Gly|Gln|Ser|Met|Gln|Val|Val|Met|Gly ( 2 ) INFORMATION FOR SEQ ID NO:3:

( i ) SEQUENCE CHARACTERISTICS:
        ( A ) LENGTH: 309 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: N. clavipes
        ( F ) TISSUE TYPE: minor ampullate gland ( i x ) FEATURE:
        ( A ) NAME/KEY: CDS
        ( B ) LOCATION: 1..309
        ( D ) OTHER INFORMATION: /product="amino terminus of MISP2
              protein"

( x i ) SEQUENCE DESCRIPTION: SEQ ID NO:3:

| TCT | TAT | GGA | CCA | TCC | GTA | TTT | TAC | ACT | CCT | ACT | TCA | GCT | GGA | AGC | TAT | 48 |
|-----|-----|-----|-----|-----|-----|-----|-----|-----|-----|-----|-----|-----|-----|-----|-----|-----|
| Ser | Tyr | Gly | Pro | Ser | Val | Phe | Tyr | Thr | Pro | Thr | Ser | Ala | Gly | Ser | Tyr | |
| 1   |     |     |     | 5   |     |     |     |     | 10  |     |     |     |     | 15  |     | |

| GGT | GCA | GGG | GCC | GGA | GGT | TTT | GGA | GCT | GGA | GCC | TCT | GCT | GGT | GTC | GGA | 96 |
|-----|-----|-----|-----|-----|-----|-----|-----|-----|-----|-----|-----|-----|-----|-----|-----|-----|
| Gly | Ala | Gly | Ala | Gly | Gly | Phe | Gly | Ala | Gly | Ala | Ser | Ala | Gly | Val | Gly | |
|     |     |     |     | 20  |     |     |     |     | 25  |     |     |     |     | 30  |     | |

| GCC | GGA | GCT | GGT | ACT | GTA | GCA | GGA | TAT | GGT | GGA | CAA | GGA | GGA | TAT | GGT | 144 |
|-----|-----|-----|-----|-----|-----|-----|-----|-----|-----|-----|-----|-----|-----|-----|-----|-----|
| Ala | Gly | Ala | Gly | Thr | Val | Ala | Gly | Tyr | Gly | Gly | Gln | Gly | Gly | Tyr | Gly | |
|     |     |     |     | 35  |     |     |     |     | 40  |     |     |     |     | 45  |     | |

| GCC | GGA | AGC | GCT | GGA | GGT | TAT | GGA | AGA | GGT | ACT | GGA | GCT | GGA | GCC | GCT | 192 |
|-----|-----|-----|-----|-----|-----|-----|-----|-----|-----|-----|-----|-----|-----|-----|-----|-----|
| Ala | Gly | Ser | Ala | Gly | Gly | Tyr | Gly | Arg | Gly | Thr | Gly | Ala | Gly | Ala | Ala | |
|     |     |     |     | 50  |     |     |     |     | 55  |     |     |     |     | 60  |     | |

| GCT | GGT | GCC | GGA | GCA | GGA | GCC | ACT | GCT | GGT | GCC | GGA | GCA | GGA | GCC | GCT | 240 |
|-----|-----|-----|-----|-----|-----|-----|-----|-----|-----|-----|-----|-----|-----|-----|-----|-----|
| Ala | Gly | Ala | Gly | Ala | Gly | Ala | Thr | Ala | Gly | Ala | Gly | Ala | Gly | Ala | Ala | |
| 65  |     |     |     |     | 70  |     |     |     |     | 75  |     |     |     |     | 80  | |

| GCT | GGT | GCC | GGA | GCA | GGA | GCA | GGT | AAT | TCA | GGA | GGA | TAT | AGT | GCC | GGA | 288 |
|-----|-----|-----|-----|-----|-----|-----|-----|-----|-----|-----|-----|-----|-----|-----|-----|-----|
| Ala | Gly | Ala | Gly | Ala | Gly | Ala | Gly | Asn | Ser | Gly | Gly | Tyr | Ser | Ala | Gly | |
|     |     |     |     | 85  |     |     |     |     | 90  |     |     |     |     | 95  |     | |

| GTA | GGA | GTT | GGT | GCT | GCA | GCT | | | | | | | | | | 309 |
|-----|-----|-----|-----|-----|-----|-----|---|---|---|---|---|---|---|---|---|-----|
| Val | Gly | Val | Gly | Ala | Ala | Ala | | | | | | | | | | |
|     |     |     | 100 |     |     |     | | | | | | | | | | |

( 2 ) INFORMATION FOR SEQ ID NO:4:

( i ) SEQUENCE CHARACTERISTICS:
        ( A ) LENGTH: 103 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ser | Tyr | Gly | Pro | Ser | Val | Phe | Tyr | Thr | Pro | Thr | Ser | Ala | Gly | Ser | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Ala | Gly | Ala | Gly | Gly | Phe | Gly | Ala | Gly | Ala | Ser | Ala | Gly | Val | Gly |
|-----|-----|-----|-----|-----|-----|-----|-----|-----|-----|-----|-----|-----|-----|-----|-----|
|     |     |     |     | 20  |     |     |     |     | 25  |     |     |     |     | 30  |     |

| Ala | Gly | Ala | Gly | Thr | Val | Ala | Gly | Tyr | Gly | Gly | Gln | Gly | Gly | Tyr | Gly |
|-----|-----|-----|-----|-----|-----|-----|-----|-----|-----|-----|-----|-----|-----|-----|-----|
|     |     |     |     | 35  |     |     |     |     | 40  |     |     |     |     | 45  |     |

| Ala | Gly | Ser | Ala | Gly | Gly | Tyr | Gly | Arg | Gly | Thr | Gly | Ala | Gly | Ala | Ala |
|-----|-----|-----|-----|-----|-----|-----|-----|-----|-----|-----|-----|-----|-----|-----|-----|
|     |     |     |     | 50  |     |     |     |     | 55  |     |     |     |     | 60  |     |

| Ala | Gly | Ala | Gly | Ala | Gly | Ala | Thr | Ala | Gly | Ala | Gly | Ala | Gly | Ala | Ala |
|-----|-----|-----|-----|-----|-----|-----|-----|-----|-----|-----|-----|-----|-----|-----|-----|

```
                      65                          70                              75                               80
Ala   Gly   Ala   Gly   Ala   Gly   Ala   Gly   Asn   Ser   Gly   Gly   Tyr   Ser   Ala   Gly
                                 85                          90                              95
Val   Gly   Val   Gly   Ala   Ala   Ala
                    100
```

( 2 ) INFORMATION FOR SEQ ID NO:5:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: N. clavipes
        ( F ) TISSUE TYPE: minor ampullate gland ( i x ) FEATURE:
        ( A ) NAME/KEY: CDS
        ( B ) LOCATION: 3..164
        ( D ) OTHER INFORMATION: /product="an internal portion of
            MISP2"

( x i ) SEQUENCE DESCRIPTION: SEQ ID NO:5:

```
CT  GCA  GCT  GCT  GGA  GGA  GGT  GCC  GGA  ACT  GTT  GGA  GGT  TAC  GGA  AGA        47
    Ala  Ala  Ala  Gly  Gly  Gly  Ala  Gly  Thr  Val  Gly  Gly  Tyr  Gly  Arg
     1              5                        10                            15

GGT  GCT  GGT  GTA  GGA  GCA  GGT  GCC  GCT  GCT  GGT  TTT  GCG  GCA  GGA  GCT        95
Gly  Ala  Gly  Val  Gly  Ala  Gly  Ala  Ala  Ala  Gly  Phe  Ala  Ala  Gly  Ala
                    20                       25                            30

GGT  GGT  GCT  GGA  GGC  TAC  AGA  AGA  GAT  GGA  GGA  TAC  GGT  GCT  GGA  GCA       143
Gly  Gly  Ala  Gly  Gly  Tyr  Arg  Arg  Asp  Gly  Gly  Tyr  Gly  Ala  Gly  Ala
               35                       40                            45

GGA  GCT  GGA  GCT  GCT  GCA  GCT  G                                                 165
Gly  Ala  Gly  Ala  Ala  Ala  Ala
          50
```

( 2 ) INFORMATION FOR SEQ ID NO:6:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Ala   Ala   Ala   Gly   Gly   Gly   Ala   Gly   Thr   Val   Gly   Gly   Tyr   Gly   Arg   Gly
 1                       5                              10                              15

Ala   Gly   Val   Gly   Ala   Gly   Ala   Ala   Ala   Gly   Phe   Ala   Ala   Gly   Ala   Gly
                    20                              25                         30

Gly   Ala   Gly   Gly   Tyr   Arg   Arg   Asp   Gly   Gly   Tyr   Gly   Ala   Gly   Ala   Gly
               35                              40                              45

Ala   Gly   Ala   Ala   Ala   Ala
               50
```

( 2 ) INFORMATION FOR SEQ ID NO:7:

( i ) SEQUENCE CHARACTERISTICS:
        ( A ) LENGTH: 870 base pairs
        ( B ) TYPE: nucleic acid
        ( C ) STRANDEDNESS: double -continued (D) TOPOLOGY: linear (ii) MOLECULE TYPE: cDNA (iii) HYPOTHETICAL: NO (vi) ORIGINAL SOURCE:
    (A) ORGANISM: N. clavipes
    (F) TISSUE TYPE: minor ampullate gland (ix) FEATURE:
    (A) NAME/KEY: CDS
    (B) LOCATION: 1..753
    (D) OTHER INFORMATION: /product="MISP2 carboxy terminus"

(xi) SEQUENCE DESCRIPTION: SEQ ID NO:7:

| GGT | GCA | GGA | GGC | TAT | GGA | AGA | GGT | GCT | GGA | GCT | GGA | GCT | GCT | GCA | GTC | 48 |
|-----|-----|-----|-----|-----|-----|-----|-----|-----|-----|-----|-----|-----|-----|-----|-----|----|
| Gly | Ala | Gly | Gly | Tyr | Gly | Arg | Gly | Ala | Gly | Ala | Gly | Ala | Ala | Ala | Val | |
| 1   |     |     |     | 5   |     |     |     |     | 10  |     |     |     |     | 15  |     | |

| GCA | GGT | GCA | GAT | GCT | GGT | GGC | TAT | GGA | AGA | AAT | TAT | GGT | GCT | GGA | ACC | 96 |
| Ala | Gly | Ala | Asp | Ala | Gly | Gly | Tyr | Gly | Arg | Asn | Tyr | Gly | Ala | Gly | Thr | |
|     |     |     | 20  |     |     |     |     | 25  |     |     |     |     | 30  |     |     | |

| ACT | GCT | TAT | GCA | GGA | GCC | AGA | GCC | GGT | GGT | GCT | GGA | GGC | TAT | GGC | GGA | 144 |
| Thr | Ala | Tyr | Ala | Gly | Ala | Arg | Ala | Gly | Gly | Ala | Gly | Gly | Tyr | Gly | Gly | |
|     |     | 35  |     |     |     |     | 40  |     |     |     |     | 45  |     |     |     | |

| CAA | GGA | GGA | TAT | TCT | TCT | GGA | GCC | GGT | GCT | GCT | GCA | GCT | TCT | GGA | GCA | 192 |
| Gln | Gly | Gly | Tyr | Ser | Ser | Gly | Ala | Gly | Ala | Ala | Ala | Ala | Ser | Gly | Ala | |
|     | 50  |     |     |     |     | 55  |     |     |     |     | 60  |     |     |     |     | |

| GGA | GCC | GAT | ATC | ACT | AGT | GGA | TAC | GGA | AGA | GGT | GTT | GGT | GCT | GGA | GCT | 240 |
| Gly | Ala | Asp | Ile | Thr | Ser | Gly | Tyr | Gly | Arg | Gly | Val | Gly | Ala | Gly | Ala | |
| 65  |     |     |     |     | 70  |     |     |     |     | 75  |     |     |     |     | 80  | |

| GGA | GCA | GAA | ACT | ATA | GGT | GCT | GGA | GGC | TAT | GGA | GGT | GGG | GCT | GGA | TCA | 288 |
| Gly | Ala | Glu | Thr | Ile | Gly | Ala | Gly | Gly | Tyr | Gly | Gly | Gly | Ala | Gly | Ser | |
|     |     |     |     | 85  |     |     |     |     | 90  |     |     |     |     | 95  |     | |

| GGA | GCA | CGT | GCG | GCT | TCA | GCA | TCC | GGA | GCT | GGT | ACT | GGA | TAT | GGT | TCG | 336 |
| Gly | Ala | Arg | Ala | Ala | Ser | Ala | Ser | Gly | Ala | Gly | Thr | Gly | Tyr | Gly | Ser | |
|     |     |     | 100 |     |     |     |     | 105 |     |     |     |     | 110 |     |     | |

| TCT | GGA | GGT | TAT | AAC | GTA | GGT | ACC | GGA | ATA | AGT | ACT | TCT | TCT | GGC | GCT | 384 |
| Ser | Gly | Gly | Tyr | Asn | Val | Gly | Thr | Gly | Ile | Ser | Thr | Ser | Ser | Gly | Ala | |
|     |     | 115 |     |     |     |     | 120 |     |     |     |     | 125 |     |     |     | |

| GCA | TCT | AGC | TAC | TCT | GTT | TCT | GCT | GGA | GGT | TAT | GCT | TCA | ACA | GGT | GTT | 432 |
| Ala | Ser | Ser | Tyr | Ser | Val | Ser | Ala | Gly | Gly | Tyr | Ala | Ser | Thr | Gly | Val | |
|     | 130 |     |     |     |     | 135 |     |     |     |     | 140 |     |     |     |     | |

| GGT | ATT | GGA | TCC | ACT | GTT | ACA | TCC | ACA | ACA | TCT | CGT | TTG | AGT | TCT | GCT | 480 |
| Gly | Ile | Gly | Ser | Thr | Val | Thr | Ser | Thr | Thr | Ser | Arg | Leu | Ser | Ser | Ala | |
| 145 |     |     |     |     | 150 |     |     |     |     | 155 |     |     |     |     | 160 | |

| GAA | GCA | TGT | TCT | AGA | ATA | TCT | GCT | GCG | GCT | TCC | ACT | TTA | GTA | TCT | GGA | 528 |
| Glu | Ala | Cys | Ser | Arg | Ile | Ser | Ala | Ala | Ala | Ser | Thr | Leu | Val | Ser | Gly | |
|     |     |     |     | 165 |     |     |     |     | 170 |     |     |     |     | 175 |     | |

| TCC | TTG | AAT | ACT | GCA | GCT | TTA | CCA | TCT | GTA | ATT | TCG | GAT | CTT | TTT | GCC | 576 |
| Ser | Leu | Asn | Thr | Ala | Ala | Leu | Pro | Ser | Val | Ile | Ser | Asp | Leu | Phe | Ala | |
|     |     |     | 180 |     |     |     |     | 185 |     |     |     |     | 190 |     |     | |

| CAA | GTT | AGT | GCA | TCA | TCA | CCC | GGG | GTA | TCA | GGT | AAC | GAA | GTT | TTG | ATT | 624 |
| Gln | Val | Ser | Ala | Ser | Ser | Pro | Gly | Val | Ser | Gly | Asn | Glu | Val | Leu | Ile | |
|     |     | 195 |     |     |     |     | 200 |     |     |     |     | 205 |     |     |     | |

| CAA | GTT | TTG | TTG | GAA | ATT | GTT | TCT | TCT | CTT | ATC | CAT | ATT | CTT | AGT | TCT | 672 |
| Gln | Val | Leu | Leu | Glu | Ile | Val | Ser | Ser | Leu | Ile | His | Ile | Leu | Ser | Ser | |
|     | 210 |     |     |     |     | 215 |     |     |     |     | 220 |     |     |     |     | |

| TCT | AGT | GTA | GGG | CAA | GTA | GAT | TTC | AGT | TCT | GTT | GGT | TCA | TCT | GCT | GCA | 720 |
| Ser | Ser | Val | Gly | Gln | Val | Asp | Phe | Ser | Ser | Val | Gly | Ser | Ser | Ala | Ala | |
| 225 |     |     |     |     | 230 |     |     |     |     | 235 |     |     |     |     | 240 | |

| GCC | GTT | GGT | CAA | TCC | ATG | CAA | GTT | GTA | ATG | GGT | TAAAACAAAA | TGGCTCTCTC | 773 |
| Ala | Val | Gly | Gln | Ser | Met | Gln | Val | Val | Met | Gly | | | |
|     |     |     |     | 245 |     |     |     |     | 250 |     | | | |

```
TCTGTTATAT GCATTCTGTA ATTTCTTCTA AACTATTAAA ATAATGTAAT AATTTCCTGC    833

ATAAATAAAA ATATTTTCT  GCAAAAAAAA AAAAAAA                             870
```

( 2 ) INFORMATION FOR SEQ ID NO:8:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Gly Ala Gly Gly Tyr Gly Arg Gly Ala Gly Ala Gly Ala Ala Val
 1               5                  10                  15

Ala Gly Ala Asp Ala Gly Gly Tyr Gly Arg Asn Tyr Gly Ala Gly Thr
             20                  25                  30

Thr Ala Tyr Ala Gly Ala Arg Ala Gly Gly Ala Gly Gly Tyr Gly Gly
         35                  40                  45

Gln Gly Gly Tyr Ser Ser Gly Ala Gly Ala Ala Ala Ser Gly Ala
     50                  55                  60

Gly Ala Asp Ile Thr Ser Gly Tyr Gly Arg Gly Val Gly Ala Gly Ala
 65                  70                  75                  80

Gly Ala Glu Thr Ile Gly Ala Gly Gly Tyr Gly Gly Gly Ala Gly Ser
             85                  90                  95

Gly Ala Arg Ala Ala Ser Ala Ser Gly Ala Gly Thr Gly Tyr Gly Ser
            100                 105                 110

Ser Gly Gly Tyr Asn Val Gly Thr Gly Ile Ser Thr Ser Ser Gly Ala
        115                 120                 125

Ala Ser Ser Tyr Ser Val Ser Ala Gly Gly Tyr Ala Ser Thr Gly Val
    130                 135                 140

Gly Ile Gly Ser Thr Val Thr Ser Thr Thr Ser Arg Leu Ser Ser Ala
145                 150                 155                 160

Glu Ala Cys Ser Arg Ile Ser Ala Ala Ala Ser Thr Leu Val Ser Gly
                165                 170                 175

Ser Leu Asn Thr Ala Ala Leu Pro Ser Val Ile Ser Asp Leu Phe Ala
            180                 185                 190

Gln Val Ser Ala Ser Ser Pro Gly Val Ser Gly Asn Glu Val Leu Ile
        195                 200                 205

Gln Val Leu Leu Glu Ile Val Ser Ser Leu Ile His Ile Leu Ser Ser
    210                 215                 220

Ser Ser Val Gly Gln Val Asp Phe Ser Ser Val Gly Ser Ser Ala Ala
225                 230                 235                 240

Ala Val Gly Gln Ser Met Gln Val Val Met Gly
                245                 250
```

( 2 ) INFORMATION FOR SEQ ID NO:9:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: N. clavipes ( F ) TISSUE TYPE: minor ampullate gland ( i x ) FEATURE:
    ( A ) NAME/KEY: -
    ( B ) LOCATION: 1..165
    ( D ) OTHER INFORMATION: /label=cloned_cDNA
        / note= "pMISS3 partial sequence, 11-1 template,
        forward primer"

( i x ) FEATURE:
    ( A ) NAME/KEY: CDS
    ( B ) LOCATION: 1..165
    ( D ) OTHER INFORMATION: /product="translation of pMISS3
        partial sequence"

( x i ) SEQUENCE DESCRIPTION: SEQ ID NO:9:

| GCT | GGA | GCT | GCT | GCT | GGT | GCT | GGA | GGC | TAT | GAC | GGA | CAA | GGA | GGA | TAT | 48 |
|-----|-----|-----|-----|-----|-----|-----|-----|-----|-----|-----|-----|-----|-----|-----|-----|----|
| Ala | Gly | Ala | Ala | Ala | Gly | Ala | Gly | Gly | Tyr | Asp | Gly | Gln | Gly | Gly | Tyr |    |
| 1   |     |     |     | 5   |     |     |     |     | 10  |     |     |     |     | 15  |     |    |

| GGT | GCT | GGA | GCA | GGA | GCT | GCT | GCA | GCT | GCT | GGA | GCA | GGA | GCC | GGA | AGC | 96 |
|-----|-----|-----|-----|-----|-----|-----|-----|-----|-----|-----|-----|-----|-----|-----|-----|----|
| Gly | Ala | Gly | Ala | Gly | Ala | Ala | Ala | Ala | Ala | Gly | Ala | Gly | Ala | Gly | Ser |    |
|     |     | 20  |     |     |     |     |     | 25  |     |     |     |     | 30  |     |     |    |

| GTT | GGA | GGT | TAT | GGA | ACA | GGT | GCT | GTA | GCT | GGA | TCT | GGA | ACA | GCT | GCT | 144 |
|-----|-----|-----|-----|-----|-----|-----|-----|-----|-----|-----|-----|-----|-----|-----|-----|-----|
| Val | Gly | Gly | Tyr | Gly | Thr | Gly | Ala | Val | Ala | Gly | Ser | Gly | Thr | Ala | Ala |     |
|     |     | 35  |     |     |     |     | 40  |     |     |     |     | 45  |     |     |     |     |

| GGT | GCA | GGA | GCC | AGA | GCT | GGT | 165 |
|-----|-----|-----|-----|-----|-----|-----|-----|
| Gly | Ala | Gly | Ala | Arg | Ala | Gly |     |
|     | 50  |     |     |     | 55  |     |     |

( 2 ) INFORMATION FOR SEQ ID NO:10:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Ala | Gly | Ala | Ala | Ala | Gly | Ala | Gly | Gly | Tyr | Asp | Gly | Gln | Gly | Gly | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Ala | Gly | Ala | Gly | Ala | Ala | Ala | Ala | Ala | Gly | Ala | Gly | Ala | Gly | Ser |
|-----|-----|-----|-----|-----|-----|-----|-----|-----|-----|-----|-----|-----|-----|-----|-----|
|     |     | 20  |     |     |     |     | 25  |     |     |     |     | 30  |     |     |     |

| Val | Gly | Gly | Tyr | Gly | Thr | Gly | Ala | Val | Ala | Gly | Ser | Gly | Thr | Ala | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Ala | Gly | Ala | Arg | Ala | Gly |
|-----|-----|-----|-----|-----|-----|-----|
|     | 50  |     |     |     | 55  |     |

( 2 ) INFORMATION FOR SEQ ID NO:11:

( i ) SEQUENCE CHARACTERISTICS:
        ( A ) LENGTH: 240 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: N. clavipes
        ( F ) TISSUE TYPE: minor ampullate gland ( i x ) FEATURE:
        ( A ) NAME/KEY: -
        ( B ) LOCATION: 1..240
        ( D ) OTHER INFORMATION: /label=cloned_cDNA
            / note= "partial sequence of pMISS3, 11-1 template,
            reverse primer"

( i x ) FEATURE:

(A) NAME/KEY: CDS
(B) LOCATION: 1..240
(D) OTHER INFORMATION: /product="pMISS3 partial sequence translation"

(xi) SEQUENCE DESCRIPTION: SEQ ID NO:11:

| | | | | | | | | | | | | | | | | |
|---|---|---|---|---|---|---|---|---|---|---|---|---|---|---|---|---|
| GGA | GCT | GCT | GCT | GGT | GCA | GGA | GCC | GGA | GCA | GGT | AGT | ACA | GGA | GGC | TTT | 48 |
| Gly | Ala | Ala | Ala | Gly | Ala | Gly | Ala | Gly | Ala | Gly | Ser | Thr | Gly | Gly | Phe | |
| 1 | | | | 5 | | | | | 10 | | | | | 15 | | |
| GGC | GGA | CAA | GGA | GGA | TAT | GGT | GCC | GGT | GCA | GGA | GCT | GCA | GCT | GCT | GGA | 96 |
| Gly | Gly | Gln | Gly | Gly | Tyr | Gly | Ala | Gly | Ala | Gly | Ala | Ala | Ala | Ala | Gly | |
| | | | 20 | | | | | 25 | | | | | 30 | | | |
| GCT | TTT | GCC | GGA | AGA | GCT | GGG | GGT | TAC | GGA | AGA | GCT | GCT | GGA | GCT | GCG | 144 |
| Ala | Phe | Ala | Gly | Arg | Ala | Gly | Gly | Tyr | Gly | Arg | Ala | Ala | Gly | Ala | Ala | |
| | | 35 | | | | | 40 | | | | | 45 | | | | |
| GCT | GGA | ACT | GGA | GCT | GCT | GCT | GGT | GCA | GGA | GCC | GGA | GCT | GGT | AGT | ACA | 192 |
| Ala | Gly | Thr | Gly | Ala | Ala | Ala | Gly | Ala | Gly | Ala | Gly | Ala | Gly | Ser | Thr | |
| | 50 | | | | | 55 | | | | | 60 | | | | | |
| GGA | GGC | TTT | GGC | GGA | CAA | AGA | GGA | TAC | GGT | GCC | GGC | AGA | AGT | AAT | GGA | 240 |
| Gly | Gly | Phe | Gly | Gly | Gln | Arg | Gly | Tyr | Gly | Ala | Gly | Arg | Ser | Asn | Gly | |
| 65 | | | | | 70 | | | | 75 | | | | | 80 | | |

(2) INFORMATION FOR SEQ ID NO:12:

(i) SEQUENCE CHARACTERISTICS:
(A) LENGTH: 80 amino acids
(B) TYPE: amino acid
(D) TOPOLOGY: linear (ii) MOLECULE TYPE: protein (xi) SEQUENCE DESCRIPTION: SEQ ID NO:12:

| | | | | | | | | | | | | | | |
|---|---|---|---|---|---|---|---|---|---|---|---|---|---|---|
| Gly | Ala | Ala | Ala | Gly | Ala | Gly | Ala | Gly | Ala | Gly | Ser | Thr | Gly | Gly | Phe |
| 1 | | | | 5 | | | | | 10 | | | | | 15 | |
| Gly | Gly | Gln | Gly | Gly | Tyr | Gly | Ala | Gly | Ala | Gly | Ala | Ala | Ala | Ala | Gly |
| | | | 20 | | | | | 25 | | | | | 30 | | |
| Ala | Phe | Ala | Gly | Arg | Ala | Gly | Gly | Tyr | Gly | Arg | Ala | Ala | Gly | Ala | Ala |
| | | 35 | | | | | 40 | | | | | 45 | | | |
| Ala | Gly | Thr | Gly | Ala | Ala | Ala | Gly | Ala | Gly | Ala | Gly | Ala | Gly | Ser | Thr |
| | 50 | | | | | 55 | | | | | 60 | | | | |
| Gly | Gly | Phe | Gly | Gly | Gln | Arg | Gly | Tyr | Gly | Ala | Gly | Arg | Ser | Asn | Gly |
| 65 | | | | | 70 | | | | 75 | | | | | 80 | |

(2) INFORMATION FOR SEQ ID NO:13:

(i) SEQUENCE CHARACTERISTICS:
(A) LENGTH: 144 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: N. clavipes
(F) TISSUE TYPE: minor ampullate gland (ix) FEATURE:
(A) NAME/KEY: -
(B) LOCATION: 1..144
(D) OTHER INFORMATION: /label=cloned_cDNA
/ note= "partial sequence of pMISS3, 11-2 template,
forward primer"

(ix) FEATURE:
(A) NAME/KEY: CDS
(B) LOCATION: 1..144
(D) OTHER INFORMATION: /product="translation of pMISS3 partial sequence"

( x i ) SEQUENCE DESCRIPTION: SEQ ID NO:13:

| TAT | GGT | GGA | CAA | GGC | GGA | TAT | GGT | GCT | GGA | GCA | GGA | GCT | GGT | GCT | GCT | 48 |
|---|---|---|---|---|---|---|---|---|---|---|---|---|---|---|---|---|
| Tyr | Gly | Gly | Gln | Gly | Gly | Tyr | Gly | Ala | Gly | Ala | Gly | Ala | Gly | Ala | Ala | |
| 1 | | | | 5 | | | | | 10 | | | | | 15 | | |

| GCA | GCC | GCA | GGA | TAT | GGA | GCC | GGT | GCT | GGA | GGA | TAC | GGT | GGA | CAA | GCT | 96 |
|---|---|---|---|---|---|---|---|---|---|---|---|---|---|---|---|---|
| Ala | Ala | Ala | Gly | Tyr | Gly | Ala | Gly | Ala | Gly | Gly | Tyr | Gly | Gly | Gln | Ala | |
| | | | 20 | | | | | 25 | | | | | 30 | | | |

| GGT | TAT | GGT | GCC | GGA | GCT | GGA | GCT | GGT | AGT | TCT | GCA | GGA | AAT | GCT | TTC | 144 |
|---|---|---|---|---|---|---|---|---|---|---|---|---|---|---|---|---|
| Gly | Tyr | Gly | Ala | Gly | Ala | Gly | Ala | Gly | Ser | Ser | Ala | Gly | Asn | Ala | Phe | |
| | | 35 | | | | | 40 | | | | | 45 | | | | |

( 2 ) INFORMATION FOR SEQ ID NO:14:

( i ) SEQUENCE CHARACTERISTICS:
    ( A ) LENGTH: 48 amino acids
    ( B ) TYPE: amino acid
    ( D ) TOPOLOGY: linear ( i i ) MOLECULE TYPE: protein ( x i ) SEQUENCE DESCRIPTION: SEQ ID NO:14:

| Tyr | Gly | Gly | Gln | Gly | Gly | Tyr | Gly | Ala | Gly | Ala | Gly | Ala | Gly | Ala | Ala |
|---|---|---|---|---|---|---|---|---|---|---|---|---|---|---|---|
| 1 | | | | 5 | | | | | 10 | | | | | 15 | |

| Ala | Ala | Ala | Gly | Tyr | Gly | Ala | Gly | Ala | Gly | Gly | Tyr | Gly | Gly | Gln | Ala |
|---|---|---|---|---|---|---|---|---|---|---|---|---|---|---|---|
| | | | 20 | | | | | 25 | | | | | 30 | | |

| Gly | Tyr | Gly | Ala | Gly | Ala | Gly | Ala | Gly | Ser | Ser | Ala | Gly | Asn | Ala | Phe |
|---|---|---|---|---|---|---|---|---|---|---|---|---|---|---|---|
| | | 35 | | | | | 40 | | | | | 45 | | | |

( 2 ) INFORMATION FOR SEQ ID NO:15:

( i ) SEQUENCE CHARACTERISTICS:
    ( A ) LENGTH: 155 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: N-terminal ( i x ) FEATURE:
    ( A ) NAME/KEY: Peptide
    ( B ) LOCATION: 1..155
    ( D ) OTHER INFORMATION: /label=MISPN_aa
      / note= "amino-terminal sequence of misp1, see Fig. 4"

( x i ) SEQUENCE DESCRIPTION: SEQ ID NO:15:

| Met | Asn | Asn | Leu | Leu | Phe | Ala | Val | Ser | Gly | Tyr | Val | Ser | Thr | Leu | Gly |
|---|---|---|---|---|---|---|---|---|---|---|---|---|---|---|---|
| 1 | | | | 5 | | | | | 10 | | | | | 15 | |

| Asn | Ala | Ile | Ser | Asp | Ala | Ser | Ala | Tyr | Ala | Asn | Ala | Leu | Ser | Ser | Ala |
|---|---|---|---|---|---|---|---|---|---|---|---|---|---|---|---|
| | | | 20 | | | | | 25 | | | | | 30 | | |

| Ile | Gly | Asn | Val | Leu | Ala | Asn | Ser | Gly | Ser | Ile | Ser | Glu | Ser | Thr | Ala |
|---|---|---|---|---|---|---|---|---|---|---|---|---|---|---|---|
| | | | 35 | | | | | 40 | | | | | 45 | | |

| Ser | Ser | Ala | Ala | Ser | Ser | Ala | Ala | Ser | Ser | Val | Thr | Thr | Thr | Leu | Thr |
|---|---|---|---|---|---|---|---|---|---|---|---|---|---|---|---|
| | 50 | | | | | 55 | | | | | 60 | | | | |

| Ser | Tyr | Gly | Pro | Ala | Val | Phe | Tyr | Ala | Pro | Ser | Ala | Ser | Ser | Gly | Gly |
|---|---|---|---|---|---|---|---|---|---|---|---|---|---|---|---|
| 65 | | | | | 70 | | | | | 75 | | | | | 80 |

| Tyr | Gly | Ala | Gly | Ala | Gly | Ala | Val | Ala | Ala | Ala | Gly | Ala | Ala | Gly | Ala |
|---|---|---|---|---|---|---|---|---|---|---|---|---|---|---|---|
| | | | | 85 | | | | | 90 | | | | | 95 | |

| Gly | Gly | Tyr | Gly | Arg | Gly | Ala | Gly | Gly | Tyr | Gly | Gly | Gln | Gly | Gly | Tyr |
|---|---|---|---|---|---|---|---|---|---|---|---|---|---|---|---|
| | | | | 100 | | | | | 105 | | | | | 110 | |

```
Gly Ala Gly Ala Gly Ala Gly Ala Ala Ala Ala Ala Gly Ala Gly Ala
            115                 120                 125
Gly Gly Ala Gly Gly Tyr Gly Arg Gly Ala Gly Ala Gly Ala Gly Ala
            130                 135                 140
Ala Ala Gly Ala Gly Ala Gly Ala Gly Gly Ala
145                 150                 155
```

( 2 ) INFORMATION FOR SEQ ID NO:16:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Peptide
        ( B ) LOCATION: 1..90
        ( D ) OTHER INFORMATION: /label=MISP2N_AA
            / note= "amino terminal peptide of MISP2, see Fig. 4"

( x i ) SEQUENCE DESCRIPTION: SEQ ID NO:16:

```
Ser Tyr Gly Pro Ser Val Phe Tyr Thr Pro Thr Ser Ala Gly Ser Tyr
1               5                   10                  15
Gly Ala Gly Ala Gly Ala Phe Gly Ala Gly Ala Ser Ala Gly Val Gly
            20                  25                  30
Ala Gly Ala Gly Thr Val Ala Gly Tyr Gly Gly Gln Gly Gly Tyr Gly
            35                  40                  45
Ala Gly Ala Gly Ser Ala Gly Gly Tyr Gly Arg Gly Thr Gly Ala Gly
            50                  55                  60
Ala Ala Ala Gly Ala Gly Ala Gly Ala Thr Ala Gly Ala Gly Ala Gly
65                  70                  75                  80
Ala Ala Ala Gly Ala Gly Ala Gly Ala Gly
            85                  90
```

( 2 ) INFORMATION FOR SEQ ID NO:17:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: peptide ( v ) FRAGMENT TYPE: C-terminal ( i x ) FEATURE:
        ( A ) NAME/KEY: Peptide
        ( B ) LOCATION: 1..115
        ( D ) OTHER INFORMATION: /label=MISP1C_AA
            / note= "carboxyl terminus of MISP1, see Fig. 4"

( x i ) SEQUENCE DESCRIPTION: SEQ ID NO:17:

```
Asp Lys Glu Ile Ala Cys Trp Ser Arg Cys Arg Tyr Thr Val Ala Ser
1               5                   10                  15
Thr Thr Ser Arg Leu Ser Ser Ala Glu Ala Ser Ser Arg Ile Ser Ser
            20                  25                  30
Ala Ala Ser Thr Leu Val Ser Gly Gly Tyr Leu Asn Thr Ala Ala Leu
            35                  40                  45
Pro Ser Val Ile Ser Asp Leu Phe Ala Gln Val Gly Ala Ser Ser Pro
            50                  55                  60
```

```
Val  Ile  Arg  Gln  Arg  Ser  Leu  Ile  Gln  Val  Leu  Leu  Glu  Ile  Val  Ser
65                       70                       75                       80

Ser  Leu  Ile  His  Ile  Leu  Ser  Ser  Ser  Val  Gly  Trp  Val  Asp  Phe
                    85                       90                       95

Ser  Ser  Val  Gly  Ser  Ser  Ala  Ala  Ala  Val  Gly  Gln  Ser  Met  Gln  Val
               100                 105                          110

Val  Met  Gly
          115
```

( 2 ) INFORMATION FOR SEQ ID NO:18:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: peptide ( v ) FRAGMENT TYPE: C-terminal ( i x ) FEATURE:
        ( A ) NAME/KEY: Peptide
        ( B ) LOCATION: 1..116
        ( D ) OTHER INFORMATION: /label=MISP2C_AA
            / note= "carboxyl terminus of MISP2, see Fig. 4"

( x i ) SEQUENCE DESCRIPTION: SEQ ID NO:18:

```
Gly  Gly  Tyr  Ala  Ser  Thr  Gly  Val  Gly  Ile  Gly  Ser  Thr  Val  Thr  Ser
1                   5                        10                       15

Thr  Thr  Ser  Arg  Leu  Ser  Ser  Ala  Glu  Ala  Cys  Ser  Arg  Ile  Ser  Ala
               20                   25                       30

Ala  Ala  Ser  Thr  Leu  Val  Ser  Gly  Gly  Ser  Leu  Asn  Thr  Ala  Ala  Leu
               35                   40                       45

Pro  Ser  Val  Ile  Ser  Asp  Leu  Phe  Ala  Gln  Val  Ser  Ala  Ser  Ser  Pro
     50                       55                       60

Gly  Val  Ser  Gly  Asn  Glu  Val  Leu  Ile  Gln  Val  Leu  Leu  Glu  Ile  Val
65                       70                       75                       80

Ser  Ser  Leu  Ile  His  Ile  Leu  Ser  Ser  Ser  Val  Gly  Gln  Val  Asp
                    85                       90                       95

Phe  Ser  Ser  Val  Gly  Ser  Ser  Ala  Ala  Ala  Val  Gly  Gln  Ser  Met  Gln
               100                 105                          110

Val  Val  Met  Gly
               115
```

( 2 ) INFORMATION FOR SEQ ID NO:19:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Peptide
        ( B ) LOCATION: 1..33
        ( D ) OTHER INFORMATION: /label=misp1_repeat
            / note= "see Table 1"

( x i ) SEQUENCE DESCRIPTION: SEQ ID NO:19:

```
Gly  Ala  Ala  Gly  Ala  Gly  Gly  Tyr  Gly  Arg  Gly  Ala  Gly  Gly  Tyr  Gly
1                   5                        10                       15

Gly  Gln  Gly  Gly  Tyr  Gly  Ala  Gly  Ala  Gly  Ala  Gly  Ala  Ala  Ala  Ala
```

Ala (2) INFORMATION FOR SEQ ID NO:20:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..51
        (D) OTHER INFORMATION: /label=misp1_repeat
            / note= "see Table 1"

(xi) SEQUENCE DESCRIPTION: SEQ ID NO:20:

```
Gly Ala Gly Ala Gly Gly Ala Gly Gly Tyr Gly Arg Gly Ala Gly Ala
 1               5                  10                   15
Gly Ala Gly Ala Ala Ala Gly Ala Gly Ala Gly Ala Gly Gly Ala Gly
                20                  25                  30
Tyr Gly Gly Gln Gly Gly Tyr Gly Ala Gly Ala Gly Ala Gly Ala Ala
            35                  40                  45
Ala Ala Ala
        50
```

(2) INFORMATION FOR SEQ ID NO:21:

(i) SEQUENCE CHARACTERISTICS:
        (A) LENGTH: 48 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..48
        (D) OTHER INFORMATION: /label=misp1_repeat
            / note= "see Table 1"

(xi) SEQUENCE DESCRIPTION: SEQ ID NO:21:

```
Gly Ala Gly Ala Gly Gly Ala Gly Gly Tyr Gly Arg Gly Ala Gly Ala
 1               5                  10                   15
Gly Ala Gly Ala Ala Ala Gly Ala Gly Ala Gly Gly Tyr Gly Gly Gln
                20                  25                  30
Gly Gly Tyr Gly Ala Gly Ala Gly Ala Gly Ala Ala Ala Ala Ala Ala
            35                  40                  45
```

(2) INFORMATION FOR SEQ ID NO:22:

(i) SEQUENCE CHARACTERISTICS:
        (A) LENGTH: 49 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..49

( D ) OTHER INFORMATION: /label=misp1_repeat
/ note= "see Table 1"

( x i ) SEQUENCE DESCRIPTION: SEQ ID NO:22:

Gly Ala Gly Ser Gly Gly Ala Gly Gly Tyr Gly Arg Gly Ala Gly Ala
1               5                   10                  15

Gly Ala Gly Ala Ala Ala Gly Ala Gly Ala Gly Ala Gly Ser Tyr Gly
                20                  25                  30

Gly Gln Gly Gly Tyr Gly Ala Gly Ala Gly Ala Gly Ala Ala Ala Ala
            35                  40                  45

Ala ( 2 ) INFORMATION FOR SEQ ID NO:23:

( i ) SEQUENCE CHARACTERISTICS:
( A ) LENGTH: 39 amino acids
( B ) TYPE: amino acid
( D ) TOPOLOGY: linear ( i i ) MOLECULE TYPE: peptide ( v ) FRAGMENT TYPE: internal ( i x ) FEATURE:
( A ) NAME/KEY: Peptide
( B ) LOCATION: 1..39
( D ) OTHER INFORMATION: /label=misp1_repeat
/ note= "see Table 1"

( x i ) SEQUENCE DESCRIPTION: SEQ ID NO:23:

Gly Ala Gly Ala Gly Gly Ala Gly Gly Tyr Gly Arg Gly Ala Gly Ala
1               5                   10                  15

Gly Ala Gly Ala Gly Ala Gly Ala Ala Ala Arg Ala Gly Ala Gly Ala
                20                  25                  30

Gly Gly Ala Ala Ala Ala Ala
            35

( 2 ) INFORMATION FOR SEQ ID NO:24:

( i ) SEQUENCE CHARACTERISTICS:
( A ) LENGTH: 47 amino acids
( B ) TYPE: amino acid
( D ) TOPOLOGY: linear ( i i ) MOLECULE TYPE: peptide ( v ) FRAGMENT TYPE: internal ( i x ) FEATURE:
( A ) NAME/KEY: Peptide
( B ) LOCATION: 1..47
( D ) OTHER INFORMATION: /label=misp1_repeat
/ note= "see Table 1"

( x i ) SEQUENCE DESCRIPTION: SEQ ID NO:24:

Gly Ala Gly Ala Gly Gly Ala Gly Gly Tyr Gly Arg Gly Ala Gly Ala
1               5                   10                  15

Gly Ala Gly Ala Ala Ala Gly Ala Gly Ala Gly Ala Gly Gly Tyr Gly
                20                  25                  30

Gly Gln Ser Gly Tyr Gly Ala Gly Ala Gly Ala Ala Ala Ala Ala
            35                  40                  45

( 2 ) INFORMATION FOR SEQ ID NO:25:

( i ) SEQUENCE CHARACTERISTICS:
( A ) LENGTH: 55 amino acids
( B ) TYPE: amino acid (D) TOPOLOGY: linear (i i) MOLECULE TYPE: peptide (v) FRAGMENT TYPE: internal (i x) FEATURE:
    (A) NAME/KEY: Peptide
    (B) LOCATION: 1..55
    (D) OTHER INFORMATION: /label=misp1_repeat
        / note= "see Table 1"

(x i) SEQUENCE DESCRIPTION: SEQ ID NO:25:

```
Gly Ala Gly Ala Gly Gly Ala Gly Gly Tyr Gly Arg Gly Ala Gly Ala
 1               5                   10                  15
Gly Ala Gly Ala Ala Ala Gly Ala Gly Ala Gly Ala Ala Ala Gly Ala
                20                  25                  30
Gly Ala Gly Gly Tyr Gly Gly Gln Gly Gly Tyr Gly Ala Gly Ala Gly
                35                  40                  45
Ala Gly Ala Ala Ala Ala Ala
         50              55
```

(2) INFORMATION FOR SEQ ID NO:26:

(i) SEQUENCE CHARACTERISTICS:
        (A) LENGTH: 47 amino acids
        (B) TYPE: amino acid
        (D) TOPOLOGY: linear (i i) MOLECULE TYPE: peptide (v) FRAGMENT TYPE: internal (i x) FEATURE:
        (A) NAME/KEY: Peptide
        (B) LOCATION: 1..47
        (D) OTHER INFORMATION: /label=misp1_repeat
            / note= "see Table 1"

(x i) SEQUENCE DESCRIPTION: SEQ ID NO:26:

```
Gly Ala Gly Ala Gly Gly Ala Gly Gly Tyr Gly Arg Gly Ala Gly Ala
 1               5                   10                  15
Gly Ala Gly Ala Ala Ala Gly Ala Gly Ala Gly Gly Tyr Gly Gly Gln
                20                  25                  30
Gly Gly Tyr Gly Ala Gly Ala Gly Ala Gly Ala Ala Ala Ala Ala
                35                  40                  45
```

(2) INFORMATION FOR SEQ ID NO:27:

(i) SEQUENCE CHARACTERISTICS:
        (A) LENGTH: 50 amino acids
        (B) TYPE: amino acid
        (D) TOPOLOGY: linear (i i) MOLECULE TYPE: peptide (v) FRAGMENT TYPE: internal (i x) FEATURE:
        (A) NAME/KEY: Peptide
        (B) LOCATION: 1..50
        (D) OTHER INFORMATION: /label=misp1_repeat
            / note= "see Table 1"

(x i) SEQUENCE DESCRIPTION: SEQ ID NO:27:

```
Thr Gly Ala Gly Gly Ala Gly Gly Tyr Gly Arg Gly Ala Gly Ala Gly
 1               5                   10                  15
Ala Gly Ala Ala Ala Gly Ala Gly Ala Gly Thr Gly Gly Ala Gly Tyr
                20                  25                  30
```

Gly Gly Gln Gly Gly Tyr Gly Ala Gly Ala Gly Ala Gly Ala Ala Ala
            35                  40                  45

Ala Ala
    50

( 2 ) INFORMATION FOR SEQ ID NO:28:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..56
        ( D ) OTHER INFORMATION: /label=misp1_repeat
            / note= "see Table 1"

( x i ) SEQUENCE DESCRIPTION: SEQ ID NO:28:

Gly Ala Gly Ala Gly Gly Ala Gly Tyr Gly Arg Gly Ala Gly Ala Gly
1               5                   10                  15

Ala Gly Ala Ala Ala Gly Ala Gly Ala Gly Ala Ala Ala Gly Ala Gly
            20                  25                  30

Ala Gly Ala Gly Gly Tyr Gly Gly Gln Gly Gly Tyr Gly Ala Gly Ala
            35                  40                  45

Arg Ala Gly Ala Ala Ala Ala Ala
    50                  55

( 2 ) INFORMATION FOR SEQ ID NO:29:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..54
        ( D ) OTHER INFORMATION: /label=misp1_repeat
            / note= "see Table 1"

( x i ) SEQUENCE DESCRIPTION: SEQ ID NO:29:

Gly Ala Gly Ala Gly Gly Ala Ala Gly Tyr Ser Arg Gly Gly Arg Ala
1               5                   10                  15

Gly Ala Ala Gly Ala Gly Ala Gly Ala Ala Ala Gly Ala Gly Ala Gly
            20                  25                  30

Ala Gly Gly Tyr Gly Gly Gln Gly Gly Tyr Gly Ala Gly Ala Gly Ala
            35                  40                  45

Gly Ala Ala Ala Ala Ala
    50

( 2 ) INFORMATION FOR SEQ ID NO:30:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: peptide (v) FRAGMENT TYPE: internal (ix) FEATURE:
    (A) NAME/KEY: Peptide
    (B) LOCATION: 1..51
    (D) OTHER INFORMATION: /label=misp1_repeat
       / note= "see Table 1"

(xi) SEQUENCE DESCRIPTION: SEQ ID NO:30:

```
Gly Ala Gly Ser Gly Gly Ala Gly Gly Tyr Gly Arg Gly Ala Gly Ala
 1               5                  10                  15
Gly Ala Ala Ala Gly Ala Gly Ala Ala Ala Gly Ala Gly Ala Gly Ala
                20                  25                  30
Gly Gly Tyr Gly Gly Gln Gly Gly Tyr Gly Ala Gly Ala Gly Ala Ala
            35                  40                  45
Ala Ala Ala
    50
```

(2) INFORMATION FOR SEQ ID NO:31:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (v) FRAGMENT TYPE: C-terminal (ix) FEATURE:
        (A) NAME/KEY: Peptide
        (B) LOCATION: 1..36
        (D) OTHER INFORMATION: /label=misp1_repeat
           / note= "see Table 1"

(xi) SEQUENCE DESCRIPTION: SEQ ID NO:31:

```
Gly Ala Gly Ala Gly Arg Gly Gly Tyr Gly Arg Gly Ala Gly Ala Gly
 1               5                  10                  15
Gly Tyr Gly Gly Gln Gly Gly Tyr Gly Ala Gly Ala Gly Ala Gly Ala
                20                  25                  30
Ala Ala Ala Ala
    35
```

(2) INFORMATION FOR SEQ ID NO:32:

(i) SEQUENCE CHARACTERISTICS:
        (A) LENGTH: 55 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..55
        (D) OTHER INFORMATION: /label=misp1_repeat
           / note= "consensus sequence of MiSP1 repeats"

(xi) SEQUENCE DESCRIPTION: SEQ ID NO:32:

```
Arg Gly Ala Ala Gly Ala Ala Gly Ala Gly Ala Gly Ala Ala Ala Gly
 1               5                  10                  15
Ala Gly Ala Gly Ala Gly Ala Gly Gly Tyr Gly Gly Gln Gly Gly Tyr
                20                  25                  30
Gly Ala Gly Ala Gly Ala Gly Ala Ala Ala Ala Ala Gly Ala Gly Ala
                35                  40                  45
```

```
Gly Gly Ala Gly Gly Tyr Gly
     50                  55
```

( 2 ) INFORMATION FOR SEQ ID NO:33:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..11
    ( D ) OTHER INFORMATION: /label=misp1_generic
      / note= "generic formula for MiSP1"

( i x ) FEATURE:
    ( A ) NAME/KEY: Duplication
    ( B ) LOCATION: 3..4
    ( D ) OTHER INFORMATION: /label=GA
      / note= "(GA) repeated 1 to 6 times"

( i x ) FEATURE:
    ( A ) NAME/KEY: Duplication
    ( B ) LOCATION: 5
    ( D ) OTHER INFORMATION: /label=A
      / note= "present as 0 to 4 residues"

( i x ) FEATURE:
    ( A ) NAME/KEY: Duplication
    ( B ) LOCATION: 6..8
    ( D ) OTHER INFORMATION: /label=GGX
      / note= "X is tyrosine, glutamine or alanine; unit
      is repeated 1 to 4 times."

( i x ) FEATURE:
    ( A ) NAME/KEY: Duplication
    ( B ) LOCATION: 9..10
    ( D ) OTHER INFORMATION: /label=GA
      / note= "repeated 1 to 6 times"

( i x ) FEATURE:
    ( A ) NAME/KEY: Duplication
    ( B ) LOCATION: 11
    ( D ) OTHER INFORMATION: /label=A
      / note= "present as 0 to 4 residues"

( x i ) SEQUENCE DESCRIPTION: SEQ ID NO:33:

```
Gly Arg Gly Ala Ala Gly Gly Xaa Gly Ala Ala
 1               5                   10
```

( 2 ) INFORMATION FOR SEQ ID NO:34:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..15
    ( D ) OTHER INFORMATION: /label=MaSP1_generic
      / note= "generic formula for MaSP1 protein (major
      ampullate spider silk protein)."

( i x ) FEATURE:
    ( A ) NAME/KEY: Duplication
    ( B ) LOCATION: 1..3

( D ) OTHER INFORMATION: /label=XGG
                            / note= "X is tyrosine or glutamine; unit is
                            repeated 2 to 3 times"

( i x ) FEATURE:
                    ( A ) NAME/KEY: Region
                    ( B ) LOCATION: 4..6
                    ( D ) OTHER INFORMATION: /label=XGA
                            / note= "X is tyrosine or glutamine; unit is
                            present once."

( i x ) FEATURE:
                    ( A ) NAME/KEY: Duplication
                    ( B ) LOCATION: 7..9
                    ( D ) OTHER INFORMATION: /label=GXG
                            / note= "X is tyrosine or glutamine; unit is
                            repeated 1 to three times."

( i x ) FEATURE:
                    ( A ) NAME/KEY: Duplication
                    ( B ) LOCATION: 10..12
                    ( D ) OTHER INFORMATION: /label=AGA
                            / note= "unit is repeated 5 to 7 times"

( i x ) FEATURE:
                    ( A ) NAME/KEY: Duplication
                    ( B ) LOCATION: 13
                    ( D ) OTHER INFORMATION: /label=G
                            / note= "present as 1 or 2 residues"

( x i ) SEQUENCE DESCRIPTION: SEQ ID NO:34:

Xaa  Gly  Gly  Xaa  Gly  Ala  Gly  Xaa  Gly  Ala  Gly  Ala  Gly  Ala  Gly
    1                   5                        10                       15

( 2 ) INFORMATION FOR SEQ ID NO:35:

( i ) SEQUENCE CHARACTERISTICS:
                    ( A ) LENGTH: 14 amino acids
                    ( B ) TYPE: amino acid
                    ( D ) TOPOLOGY: linear ( i i ) MOLECULE TYPE: peptide ( v ) FRAGMENT TYPE: internal ( i x ) FEATURE:
                    ( A ) NAME/KEY: Peptide
                    ( B ) LOCATION: 1..14
                    ( D ) OTHER INFORMATION: /label=MaSP2_generic
                            / note= "generic formula for MaSP2 protein (major
                            ampullate spider silk protein)."

( i x ) FEATURE:
                    ( A ) NAME/KEY: Duplication
                    ( B ) LOCATION: 1..10
                    ( D ) OTHER INFORMATION: /label=GPG2YGPGQ2
                            / note= "unit is repeated 2 or 3 times"

( i x ) FEATURE:
                    ( A ) NAME/KEY: Duplication
                    ( B ) LOCATION: 11..12
                    ( D ) OTHER INFORMATION: /label=XX
                            / note= "X is GPG or GPS"

( i x ) FEATURE:
                    ( A ) NAME/KEY: Duplication
                    ( B ) LOCATION: 14
                    ( D ) OTHER INFORMATION: /label=A
                            / note= "present as 7 to 10 residues"

( x i ) SEQUENCE DESCRIPTION: SEQ ID NO:35:

Gly  Pro  Gly  Gly  Tyr  Gly  Pro  Gly  Gln  Gln  Xaa  Xaa  Ser  Ala
    1                   5                        10

( 2 ) INFORMATION FOR SEQ ID NO:36:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( v ) FRAGMENT TYPE: internal ( i x ) FEATURE:
  ( A ) NAME/KEY: Peptide
  ( B ) LOCATION: 1..6
  ( D ) OTHER INFORMATION: /label=MiSP_simple
    / note= "simplified MiSP1 generic formula; x is tyrosine, glutamine or alan..."

( i x ) FEATURE:
  ( A ) NAME/KEY: Duplication
  ( B ) LOCATION: 1..3
  ( D ) OTHER INFORMATION: /label=GGX
    / note= "X is tyrosine, glutamine or alanine; unit is repeated 1 to 4 times."

( i x ) FEATURE:
  ( A ) NAME/KEY: Duplication
  ( B ) LOCATION: 4..5
  ( D ) OTHER INFORMATION: /label=GA
    / note= "unit is present 0 to 4 times"

( i x ) FEATURE:
  ( A ) NAME/KEY: Duplication
  ( B ) LOCATION: 6
  ( D ) OTHER INFORMATION: /label=A
    / note= "present as 1 to 6 residues"

( x i ) SEQUENCE DESCRIPTION: SEQ ID NO:36:

Gly Gly Xaa Gly Ala Ala
1                5

( 2 ) INFORMATION FOR SEQ ID NO:37:

( i ) SEQUENCE CHARACTERISTICS:
    ( A ) LENGTH: 47 amino acids
    ( B ) TYPE: amino acid
    ( D ) TOPOLOGY: linear ( i i ) MOLECULE TYPE: peptide ( v ) FRAGMENT TYPE: N-terminal ( i x ) FEATURE:
    ( A ) NAME/KEY: Peptide
    ( B ) LOCATION: 1..47
    ( D ) OTHER INFORMATION: /label=MaSP2_repeat
      / note= "see Table 2"

( x i ) SEQUENCE DESCRIPTION: SEQ ID NO:37:

Gly Pro Gly Gln Gln Gly Pro Gly Gly Tyr Gly Pro Gly Gln Gln Gly
1                5                   10                  15

Pro Ser Gly Pro Gly Ser Ala Ala Ala Ala Ala Ala Ala Ala Ala Ala
            20                  25                  30

Gly Pro Gly Gly Tyr Gly Pro Gly Gln Gln Gly Pro Gly Gly Tyr
        35                  40                  45

( 2 ) INFORMATION FOR SEQ ID NO:38:

( i ) SEQUENCE CHARACTERISTICS:
    ( A ) LENGTH: 38 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..38
    ( D ) OTHER INFORMATION: /label=MaSP2_repeat
        / note= "see Table 2"

( x i ) SEQUENCE DESCRIPTION: SEQ ID NO:38:

```
Gly Pro Gly Gln Gln Gly Pro Gly Arg Tyr Gly Pro Gly Gln Gln Gly
 1               5                  10                  15

Pro Ser Gly Pro Gly Ser Ala Ala Ala Ala Ala Ala Gly Ser Gly Gln
            20                  25                  30

Gln Gly Pro Gly Gly Tyr
            35
```

( 2 ) INFORMATION FOR SEQ ID NO:39:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..52
        ( D ) OTHER INFORMATION: /label=MaSP2_repeat
            / note= "see Table 2"

( x i ) SEQUENCE DESCRIPTION: SEQ ID NO:39:

```
Gly Pro Arg Gln Gln Gly Pro Gly Gly Tyr Gly Gln Gly Gln Gln Gly
 1               5                  10                  15

Pro Ser Gly Pro Gly Ser Ala Ala Ala Ala Ser Ala Ala Ala Ser Ala
            20                  25                  30

Glu Ser Gly Gln Gln Gly Pro Gly Gly Tyr Gly Pro Gly Gln Gln Gly
            35                  40                  45

Pro Gly Gly Tyr
        50
```

( 2 ) INFORMATION FOR SEQ ID NO:40:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..40
        ( D ) OTHER INFORMATION: /label=MaSP2_repeat
            / note= "see Table 2"

( x i ) SEQUENCE DESCRIPTION: SEQ ID NO:40:

```
Gly Pro Gly Gln Gln Gly Pro Gly Gly Tyr Gly Pro Gly Gln Gln Gly
 1               5                  10                  15

Pro Ser Gly Pro Gly Ser Ala Ala Ala Ala Ala Ala Ala Ser Gly Pro
            20                  25                  30

Gly Gln Gln Gly Pro Gly Gly Tyr
            35                  40
```

( 2 ) INFORMATION FOR SEQ ID NO:41:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..41
        ( D ) OTHER INFORMATION: /label=MaSP2_repeat
            / note= "see Table 2"

( x i ) SEQUENCE DESCRIPTION: SEQ ID NO:41:

```
Gly Pro Gly Gln Gln Gly Pro Gly Gly Tyr Gly Pro Gly Gln Gln Gly
 1               5                  10                  15
Pro Ser Gly Pro Gly Ser Ala Ala Ala Ala Ala Ala Ala Ala Ser Gly
            20                  25                  30
Pro Gly Gln Gln Gly Pro Gly Gly Tyr
            35                  40
```

( 2 ) INFORMATION FOR SEQ ID NO:42:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..29
        ( D ) OTHER INFORMATION: /label=MaSP2_repeat
            / note= "see Table 2"

( x i ) SEQUENCE DESCRIPTION: SEQ ID NO:42:

```
Gly Pro Gly Gln Gln Gly Pro Gly Gly Tyr Gly Pro Gly Gln Gln Gly
 1               5                  10                  15
Leu Ser Gly Pro Gly Ser Ala Ala Ala Ala Ala Ala Ala
            20                  25
```

( 2 ) INFORMATION FOR SEQ ID NO:43:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..36
        ( D ) OTHER INFORMATION: /label=MaSP2_repeat
            / note= "see Table 2"

( x i ) SEQUENCE DESCRIPTION: SEQ ID NO:43:

```
Gly Pro Gly Gln Gln Gly Pro Gly Gly Tyr Gly Pro Gly Gln Gln Gly
 1               5                  10                  15
Pro Ser Gly Pro Gly Ser Ala Ala Ala Ala Ala Ala Ala Ala Gly
            20                  25                  30
```

```
        Pro Gly Gly Tyr
                35
```

(2) INFORMATION FOR SEQ ID NO:44:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..39
        (D) OTHER INFORMATION: /label=MaSP2_repeat
            / note= "see Table 2"

(xi) SEQUENCE DESCRIPTION: SEQ ID NO:44:

```
Gly Pro Gly Gln Gln Gly Pro Gly Gly Tyr Gly Pro Gly Gln Gln Gly
 1               5                  10                  15

Pro Ser Gly Ala Gly Ser Ala Ala Ala Ala Ala Ala Ala Gly Pro Gly
            20                  25                  30

Gln Gln Gly Leu Gly Gly Tyr
            35
```

(2) INFORMATION FOR SEQ ID NO:45:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..32
        (D) OTHER INFORMATION: /label=MaSP2_repeat
            / note= "see Table 2"

(xi) SEQUENCE DESCRIPTION: SEQ ID NO:45:

```
Gly Pro Gly Gln Gln Gly Pro Gly Gly Tyr Gly Pro Gly Gln Gln Gly
 1               5                  10                  15

Pro Gly Gly Tyr Gly Pro Gly Ser Ala Ser Ala Ala Ala Ala Ala Ala
            20                  25                  30
```

(2) INFORMATION FOR SEQ ID NO:46:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..37
        (D) OTHER INFORMATION: /label=MaSP2_repeat
            / note= "see Table 2"

(xi) SEQUENCE DESCRIPTION: SEQ ID NO:46:

```
Gly Pro Gly Gln Gln Gly Pro Gly Gly Tyr Gly Pro Gly Gln Gln Gly
 1               5                  10                  15
```

Pro Ser Gly Pro Gly Ser Ala Ser Ala Ala Ala Ala Ala Ala Ala
            20              25                      30

Gly Pro Gly Gly Tyr
            35

( 2 ) INFORMATION FOR SEQ ID NO:47:

( i ) SEQUENCE CHARACTERISTICS:
      ( A ) LENGTH: 37 amino acids
      ( B ) TYPE: amino acid
      ( D ) TOPOLOGY: linear ( i i ) MOLECULE TYPE: peptide ( v ) FRAGMENT TYPE: internal ( i x ) FEATURE:
      ( A ) NAME/KEY: Peptide
      ( B ) LOCATION: 1..37
      ( D ) OTHER INFORMATION: /label=MaSP2_repeat
                / note= "see Table 2"

( x i ) SEQUENCE DESCRIPTION: SEQ ID NO:47:

Gly Pro Gly Gln Gln Gly Pro Gly Gly Tyr Ala Pro Gly Gln Gln Gly
1               5                   10                  15

Pro Ser Gly Pro Gly Ser Ala Ser Ala Ala Ala Ala Ala Ala Ala Ala
            20              25                      30

Gly Pro Gly Gly Tyr
            35

( 2 ) INFORMATION FOR SEQ ID NO:48:

( i ) SEQUENCE CHARACTERISTICS:
      ( A ) LENGTH: 36 amino acids
      ( B ) TYPE: amino acid
      ( D ) TOPOLOGY: linear ( i i ) MOLECULE TYPE: peptide ( v ) FRAGMENT TYPE: C-terminal ( i x ) FEATURE:
      ( A ) NAME/KEY: Peptide
      ( B ) LOCATION: 1..36
      ( D ) OTHER INFORMATION: /label=MaSP2_repeat
                / note= "see Table 2"

( x i ) SEQUENCE DESCRIPTION: SEQ ID NO:48:

Gly Pro Gly Gln Gln Gly Pro Gly Gly Tyr Ala Pro Gly Gln Gln Gly
1               5                   10                  15

Pro Ser Gly Pro Gly Ser Ala Ala Ala Ala Ala Ala Ala Ser Ala Gly
            20              25                      30

Pro Gly Gly Tyr
            35

( 2 ) INFORMATION FOR SEQ ID NO:49:

( i ) SEQUENCE CHARACTERISTICS:
      ( A ) LENGTH: 37 amino acids
      ( B ) TYPE: amino acid
      ( D ) TOPOLOGY: linear ( i i ) MOLECULE TYPE: peptide ( v ) FRAGMENT TYPE: internal ( i x ) FEATURE:
      ( A ) NAME/KEY: Peptide
      ( B ) LOCATION: 1..37

(D) OTHER INFORMATION: /label=MaSP2_consensus
/ note= "consensus sequence of MaSP2 repeat units"

(xi) SEQUENCE DESCRIPTION: SEQ ID NO:49:

Gly Pro Gly Gln Gln Gly Pro Gly Gly Tyr Gly Pro Gly Gln Gln Gly
1               5                   10                  15

Pro Ser Gly Pro Gly Ser Ala Ala Ala Ala Ala Ala Ala Ala Ala Ala
            20                  25                  30

Gly Pro Gly Gly Tyr
            35

(2) INFORMATION FOR SEQ ID NO:50:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: -
        (B) LOCATION: 1..84
        (D) OTHER INFORMATION: /label=oligonucleotide
            / note= "S2 long oligo"

(xi) SEQUENCE DESCRIPTION: SEQ ID NO:50:

TCTAGCCCGG GTGGCTATGG TCCTGGACAG CAAGGTCCTG GCGGTTACGG TCCTGGCCAA    60

CAGGGTCCCT CTGGTCCAGG CAGT    84

(2) INFORMATION FOR SEQ ID NO:51:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..59
        (D) OTHER INFORMATION: /label=oligonucleotide
            / note= "S2 short oligo"

(xi) SEQUENCE DESCRIPTION: SEQ ID NO:51:

TCCGGACCTG CTGCGGCGGC TGCGGCAGCT GCACTGCCTG GACCAGAGGG ACCCTGTTG    59

(2) INFORMATION FOR SEQ ID NO:52:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..35
        (D) OTHER INFORMATION: /label=MaSP2_repeat
            / note= "basic repeat unit of MaSP2 protein"

(xi) SEQUENCE DESCRIPTION: SEQ ID NO:52:

| Pro | Gly | Gly | Tyr | Gly | Pro | Gly | Gln | Gln | Gly | Pro | Gly | Gly | Tyr | Gly | Pro |
| 1 | | | | 5 | | | | | 10 | | | | | 15 | |
| Gly | Gln | Gln | Gly | Pro | Ser | Gly | Pro | Gly | Ser | Ala | Ala | Ala | Ala | Ala | Ala |
| | | | 20 | | | | | 25 | | | | | 30 | | |
| Ala | Ala | Gly | | | | | | | | | | | | | |
| | | 35 | | | | | | | | | | | | | |

( 2 ) INFORMATION FOR SEQ ID NO:53:

( i ) SEQUENCE CHARACTERISTICS:
    ( A ) LENGTH: 13 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i x ) FEATURE:
    ( A ) NAME/KEY: -
    ( B ) LOCATION: 1..13
    ( D ) OTHER INFORMATION: /label=enzyme_site
        / note= "generic recognition site for Sfi I
        restriction enzyme"

( x i ) SEQUENCE DESCRIPTION: SEQ ID NO:53:

GGCCNNNNNG GCC 13

( 2 ) INFORMATION FOR SEQ ID NO:54:

( i ) SEQUENCE CHARACTERISTICS:
    ( A ) LENGTH: 13 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: -
    ( B ) LOCATION: 1..13
    ( D ) OTHER INFORMATION: /label=Sfi_I_site
        / note= "top strand of synthetic Sfi I/AlwN I
        linker"

( x i ) SEQUENCE DESCRIPTION: SEQ ID NO:54:

GGCCGCAGCG GCC 13

( 2 ) INFORMATION FOR SEQ ID NO:55:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..4
    ( D ) OTHER INFORMATION: /label=linker_peptide
        / note= "amino acids encoded by Sfi I/AlwN I
        linker"

( x i ) SEQUENCE DESCRIPTION: SEQ ID NO:55:

Ala Ala Ala Ala
1

(2) INFORMATION FOR SEQ ID NO:56:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..6
        (D) OTHER INFORMATION: /label=NBS_peptides
        / note= "see discussion page 13"

(xi) SEQUENCE DESCRIPTION: SEQ ID NO:56:

Gly Gly Gln Gly Gly Tyr
1                 5

MINOR AMPULLATE SPIDER SILK PROTEINS

This application is a divisional of Ser. No. 08/209,747, filed Mar. 14, 1994.

RELATED APPLICATIONS

The present application is related to copending application U.S. Ser. No. 07/684,819, filed Apr. 15, 1991, the entire contents of which are hereby incorporated by reference.

FIELD OF THE INVENTION

The present invention relates to polypeptides that form macroscopic fibers and to cloned DNA encoding such polypeptides.

The proteins are some of those which constitute silks made by spiders. Preferred embodiments of the present invention are those silk proteins made in the minor ampullate glands of the spider *Nephila clavipes*. The silks of the present invention also encompass fibers made from synthetic polypeptides of amino acid sequences derivable from the amino acid sequence of the *N. clavipes* ampullate silks or made from polypeptides expressed from cloned DNA obtained from a library of spider complementary or genomic DNA.

BACKGROUND OF THE INVENTION

The orb web spiders (Nephila) possess six types of silk synthetic glands, two of which are the major and minor ampullate organs. The major and minor ampullate silks are distinguishable by their physical and chemical properties.

The major ampullate (dragline) silk possesses unique physical properties, combining high tensile strength and substantial elasticity [Denny, M. W. *J. Exp. Biol.*, 65, 483–506(1976); Lucas, F. Discovery, 25, 20–26 (1964)]. Previous investigations suggest that spider silk is composed of a single large protein, primarily containing pseudo-crystalline regions of stack β-pleated sheet alternating with amorphous domains. [Warwicker, J. O., *J.Mol.Biol.*, 2, 350–362 (1960); Lucase, F. et al, *J.Text Inst.*, 46, T440–T452 (1985); Hepburn, H. R. et al., *Insect Biochem.*, 9, 69–71 (1979)].

In fact, the major ampullate silk of *Nephila clavipes* was found to be composed of a composite of two proteins. cDNA clones encoding both of the proteins comprising the major ampullate silk are described in copending application U.S. Ser. No. 07/684,819. We describe herein the isolation and characterization of cDNA clones encoding proteins composing minor ampullate silk.

SUMMARY OF THE INVENTION

Spider silk is composed of fibers formed from proteins. We have found that natural spider silk fibers are composites of two or more proteins. However, it is possible to form fibers from a single spider silk protein. In general, spider silk proteins are found to have primary amino acid sequences that can be characterized as indirect repeats of a short consensus sequence. Variation in the consensus sequence is then responsible for the distinguishable properties of the different silks proteins.

Furthermore, silk fibers can be made from synthetic polypeptides having amino acid sequences substantially similar to the consensus repeat unit of a silk protein or from polypeptides expressed from cloned DNA encoding a natural or engineered silk protein.

Thus, it is one object of the present invention to provide cloned DNA which encodes a spider silk protein. The cloned DNA is preferably obtained from an orb web spider (Nephila). Cloned cDNA from the minor ampullate gland of *Nephila clavipes* is described in detail below.

Naturally occurring spider silk proteins have an imperfectly repetitive structure. However, the imperfection in the repetition is likely to be a consequence of the process by which the silk protein genes evolved, rather than a requirement for fiber formation. The imperfection in repetition is thus likely to only subtly affect the characteristics of the fibers which form from the aggregation of the protein molecules. Accordingly, it is a second object of the present invention to provide cloned DNA encoding an engineered spider silk protein comprising a polypeptide having direct repeats of a unit amino acid sequence. Alternatively, the cDNA may include several different unit amino acid sequences to form a "copolymer" silk protein.

It is a third object of the invention to provide a spider silk protein expressed from a cloned DNA, wherein the cloned DNA is either one obtained from a spider ampullate gland cDNA, a genomic DNA, or synthetic DNA.

Finally, it is an additional object of the present invention to provide fibers made from silk protein obtained by expression of cloned DNA.

BRIEF DESCRIPTION OF THE DRAWINGS

FIG. 1A–1F shows the nucleotide and the amino acid sequence translation of the insert from pMISS1 (SEQ. ID. NOS.:1 and 2).

FIG. 2A–2D shows the nucleotide and the amino acid sequence translation of the portions of the insert from pMISS2 that have been sequenced. 2A shows 309 nucleotides at the 5' end of pMISS2 (SEQ. ID. NO.:3). 2B shows 165 nucleotides of the PstI fragment (SEQ. ID. NO.:5) (see FIG. 4). 2C, 2D show the 870 nucleotides at the 3' end of the insert in pMISS2 (SEQ. NO. ID.:7).

FIG. 3A–3C shows the nucleotide and the amino acid sequence translation of the portions of the inserts from the 11-1 and 11-2 clones (pMISS3) that have been sequenced. 3A shows 165 nucleotides from the forward primer of the 11-1 clone (SEQ. ID. NOS.:9–10). 3B shows 240 nucleotides from the reverse primer of the 11-1 clone (SEQ. ID. NOS.:11–12). 3C shows 146 nucleotides from the forward primer of the 11-2 clone (SEQ. ID. NOS.:13–14).

FIG. 4 shows the alignment of the amino acid sequences of the nonrepetitive regions of MiSP1 and MiSP2 (SEQ. ID. NO.:15–18).

DETAILED DESCRIPTION OF THE INVENTION

Figure 5:
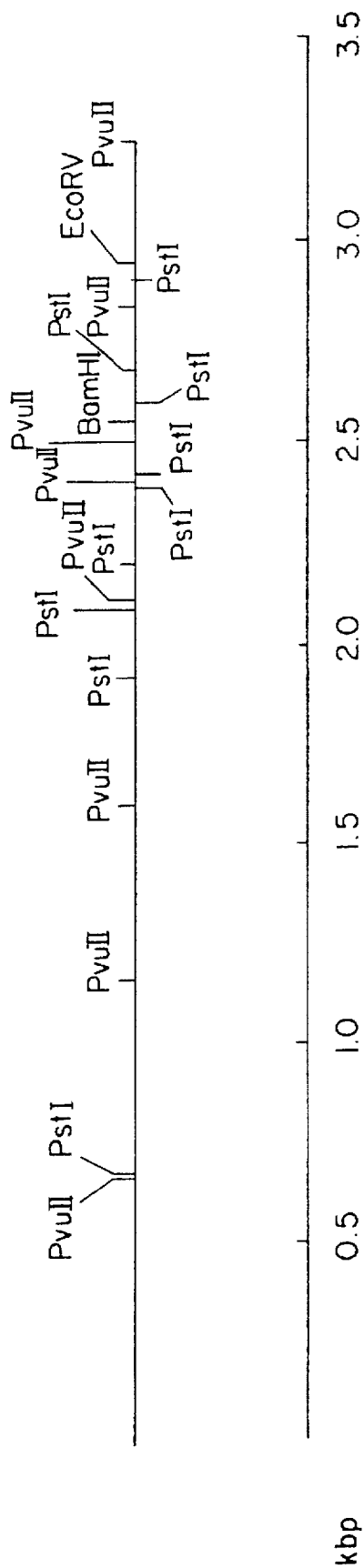
FIG. 5 shows a restriction map of the pMISS1 insert cDNA.

Studies in our laboratory have established that the major ampullate silk is composed of two distinct proteins. The major ampullate silk proteins possess the secondary structure predicted by Warwicker and others. The primary structure of the major ampullate silk proteins is characterized by indirect repeat of a discrete repeat unit. The sequence of the repeat unit is different for each of the proteins comprising the major ampullate silk.

The Nephila minor ampullate silk can be distinguished from the Nephila major ampullate silk by both physical and chemical properties. In contrast to the elasticity exhibited by the major ampullate silk, the minor ampullate silk is observed to yield without recoil. The minor silk will stretch about 25% of its initial length before breaking, exhibiting a tensile strength of nearly 100,000 psi. The amino acid composition of solubilized minor ampullate silk also differs from that of solubilized major ampullate silk.

Like the major ampullate silk proteins (major spidroin 1, MaSP1; major spidroin 2, MaSP2), the proteins comprising minor ampullate silk are found to have a primary structure dominated by imperfect repetition of a short sequence of amino acids. A "unit repeat" constitutes one such short sequence. Thus, the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein. However, synthetic spider silks can be made wherein the primary structure of the protein can be described as a number of exact repetitions of a single unit repeat. Additional synthetic spider silks can be described as a number of repetitions of one unit repeat together with a number of repetitions of a second unit repeat. Such a structure would be similar to a typical block copolymer. Of course, unit repeats of several different sequences can also be combined Spider Silk Protein 1 and spider silk Protein 2 may each have 900 to 2700 amino acids with 25 to 100, preferably 30 to 90 repeats. The spider silk or fragment or variant thereof usually has a molecular weight of at least about 16,000 daltons, preferably 16,000 to 100,000 daltons, more preferably 50,000 to 80,000 daltons for fragments and greater than 100,000 but less than 300,000 daltons, preferably 120,000 to 300,000 for the full length protein.

An alternative way to describe the primary structure of spider silk proteins is to consider a "consensus" sequence that is derived from an alignment of the unit repeats. Such a consensus sequence is the length of most of the unit repeats and accounts for the variation at each position of the unit repeat by including the residue most common at each position. For the MaSP2 protein, the consensus sequence derived is GPGQQGPGGYGPGQQGPSGPG-SAAAAAAAAAAGPGGY (SEQ. ID. NO.:49) (Table 2).

Cloned DNA of the present invention includes sequences shown in FIGS. 1A–1F, 2A–2C and 3A–3C. The cloned DNA of the present invention also includes DNA molecules made from Nephila DNA or RNA templates by PCR or the like, using primers made from sequences shown in FIGS. 1A–1F, 2A–2C and 3A–3C. Finally, cloned DNA of the present invention also encompasses polynucleotides which can hybridize to DNA having sequences shown in FIGS. 1A–1F, 2A–2C and 3A–3C under hybridization conditions typically used for library screening and Southern blotting. Preferably such hybridization conditions are those obtained by a solution of 6×SSC or SSPE, 5×Denhardt's solution, 0.5% SDS at a temperature of about 68° C., or those obtained by the same solution that is also 50% in formamide at a temperature of about 42° C. Alternatively, the hybridization conditions are those wherein the temperature is about 15°–20° C. below the $T_m$ calculated for the solution conditions. [See, J. Sambrook et al., *Molecular Cloning: A Laboratory Manual*, 2nd ed., pp. 9.47–9.58, c. 1989 by Cold Spring Harbor Laboratory press, Cold Spring Harbor, N.Y.].

The polypeptides of the present invention can be made by direct synthesis or by expression from cloned DNA. The means for expressing cloned DNA are generally known in the art. However, there are some considerations for design of expression vectors that are unusual for expressing DNA encoding the spider silk proteins of the present invention.

First, the proteins are highly repetitive in their structure. Accordingly, cloned DNA should be propagated and expressed in host cell strains that will maintain repetitive sequences in extrachromosomal elements (e.g. SURE™ cells, Stratagene). Also, due to the high content of alanine, glycine, proline, and glutamine, it might be advantageous to use a host cell which overexpresses tRNA for these amino acids.

The proteins of the present invention can otherwise be expressed using vectors providing for high level transcription, fusion proteins allowing affinity purification through an epitope tag, and the like. The hosts can be either bacterial or eukaryotic. It is considered that yeast, especially *Saccharomyces cerevisisae*, or insect cells might be advantageous eukaryotic hosts.

Fibrillar aggregates will form by spontaneous self-assembly of spider silk proteins when the protein concentration exceeds a critical value. The aggregates can be gathered and mechanically spun into macroscopic fibers according to the method of O'Brien et al. [I. O'Brien et al., "Design, Synthesis and Fabrication of Novel Self-Assembling Fibrillar Proteins", in *Silk Polymers: Materials Science and Biotechnology*, pp. 104–117, Kaplan, Adams, Farmer and Viney, eds., c. 1994 by American Chemical Society, Washington, D.C.].

The following examples are provided to illustrate the invention in more detail. The examples are not to be taken as limiting the invention, the scope of which is rather defined by the claims following.

EXAMPLE I cDNA Clones Encoding Minor Ampullate Silk Proteins

The minor ampullate glands are small, J-shaped organs located in the abdomen of the spider. The minor ampullate glands (about 20) were removed from a number of spiders and frozen in liquid nitrogen. Total RNA was prepared from the frozen tissue by standard methods. cDNA was prepared from the total RNA using the RIBOCLONE™ system (Promega). The synthesis method was modified slightly by using pseudorandom hexamers in addition to the NotI primer-adapter in the primer extension steps. The pseudorandom hexamers were synthesized having the sequence (A or T) (G or C) (G or C)(A or T)(G or C)(G or C). Such hexamers reflect the sequence bias in the minor ampullate silk proteins (minor spidroins, MiSP) we hypothesized would be imposed by repetition of alanine and glycine residues, which are found in large proportion in the amino acid composition of solubilized minor ampullate silk. We anticipated that so biasing the primer composition would enrich the library in long cDNAs encoding MiSp proteins.

The cDNA thus synthesized was ligated to appropriately digested pGEM3Zf(−) plasmid (Promega) and the ligation mixture was used to transform SURE™ *E. Coli* cells (Stratagene). Plasmid DNA was prepared from randomly selected transformed colonies and the insert DNA was partially sequenced, using the forward and reverse primers provided by the supplier (Promega), that are complementary to the vector sequence near the insert. Clones having inserts encoding highly repetitive sequences were examined in greater detail with respect to insert size. Clones having an insert size greater than 1.5 kbp were sequenced in their entirety.

The entire insert of the pMISS1 (encoding MiSP1) has been sequenced. The nucleotide sequence and the resulting translation are shown in FIGS. 1A–1F. A restriction map is shown as FIG. 5. The region from nucleotides 96–137 is represented as indeterminate. That portion of the cDNA is found to have a much higher GC content than the remainder of the sequence. As a result, that portion of the nucleotide sequence has not been resolved due to "compression" observed in the electrophoresis step. pMISS1 contains an open reading frame beginning with the ATG start codon at nucleotides 183–185. The open reading frame encodes a 5'-nonrepetitive region, an indirect repetitive region and a 3'-nonrepetitive region. The 5'-nonrepetitive region contains a sequence of about 16 residues (amino acids 2–17) that conforms to secretion signal sequences. The presence of the leader peptide suggests that the MiSP1 protein is processed and secreted through the endoplasmic reticulum.

Table 1 shows the MiSP1 amino acid sequence formatted to show the 13 unit repeats (SEQ. ID. NO.:32) of the MiSP1 protein.

MaSP1 (SEQ. ID. NO.:34)

$$(XGG)_w(XGA)(GXG)_x(AGA)_y(G)_zAG$$

where X is tyrosine or glutamine
and where w=2–3, x=1–3, y=5–7, and z=1 or 2.
MaSP2 (SEQ. ID. NO.:35)

$$(GPG_2YGPGQ_2)_a(X)_2S(A)_b$$

where X=GPG or GPS
and where a=2 or 3 and b=7 to 10.

Inspection of the amino acid sequence of MiSP1 shows that, for the most part, the protein can be viewed as a derivatized polyamide. Accordingly, a polypeptide having the less complex generic formula (SEQ. ID. NO.:36)

$$(GGX)_n(GA)_m(A)_l$$

where X is tyrosine, glutamine or alanine and
where l=1 to 6, m=0 to 4 and n=1 to 4,
would also be expected to have many of the properties of the MiSP1 protein.

The 3'-nonrepetitive coding region of pMISS1 encodes a 96 amino acid spider silk consensus sequence that is 50%

TABLE 1

Minor Ampullate Spidroin 1 Residues 92-706, showing alignment of unit repeats:

```
GAAGAGGYGRGAG--------------GYGGQGGYGAGAGAGAAAAA
GAGAGGAGGYGRGAGAGAGAAAGAGAGAGGAGYGGQGGYGAGAGAGAAAAA
GAGAGGAGGYGRGAGAGAGAAAGAGA----GGYGGQGGYGAGAGAGAAAAA
GAGSGGAGGYGRGAGAGAGAAAGAGAGA--GSYGGQGGYGAGAGAGAAAAA
GAGAGGAGGYGRGAGAGAGAGAGAAARAGAGAGG----------AAAAA
GAGAGGAGGYGRGAGAGAGAAAGAGAGA------GGYGGQSGYGAGAG--AAAAA
GAGAGGAGGYGRGAGAGAGAAAGAGAGAAAGAGAGGYGGQGGYGAGAGAGAAAAA
GAGAGGAGGYGRGAGAGAGAAAGAGAG---GYGGQGGYGAGAGAGAAAAA
-TGAGGAGGYGRGAGAGAGAAAGAGAGTGGAGYGGQGGYGAGAGAGAAAAA
GAGAGGAG-YGRGAGAGAGAAAGAGAGAAAGAGAGAGGYGGQGGYGAGARAGAAAAA
GAGAGGAAGYSRGGRAGAAGAGAAAAGAGAGAGGYGGQGGYGAGAGAGAAAAA
GAGSGGAGGYGRGAGAGAAAGAGAAAGAGAGAGGYGGQGGYGAGAGAAAAA
GAGAGRGGYGRGAGAGGYGGQGGYGAGAGAGAAAAA
```

- added for purposes of alignment

Each repeat is a variation of the consensus amino acid sequence (SEQ. ID. NO.:32) RGAAGAAGAGAGAAA-G A G A G A G A G G Y G G Q G G Y G - AGAGAGAAAAGAGAGGAGGYG. This repetitive region can be described as a mixture of two types of units, (1) dimers of alanine separated by glycine residues, and (2) dimers of glycine separated by tyrosine or glutamine residues. It is thus distinguishable from the consensus sequence of the MaSP2 protein, which can be characterized as predominantly dimers of glycine or glutamine separated by proline or tyrosine residues.

Alternatively, the majority of the amino acid sequence of the MiSP1 protein can be described by a repeat unit having the generic formula (SEQ. ID. NO.:33)

$$(GR)(GA)_1(A)_m(GGX)_n(GA)_l(A)_m$$

where X is tyrosine, glutamine or alanine and where l=1 to 6, m=0 to 4 and n=1 to 4.
This finding is similar to what was observed for the MaSP1 and MaSP2 proteins, which exhibit the generic formulas:

and 49% identical to the 3'-nonrepetitive regions of MaSP1 and MaSP2, respectively. The coding region ends at nucleotide position 2634 with a TAA stop codon. The 3' untranslated region of pMISS1 contains a poly(A) tail.

Figure 6:
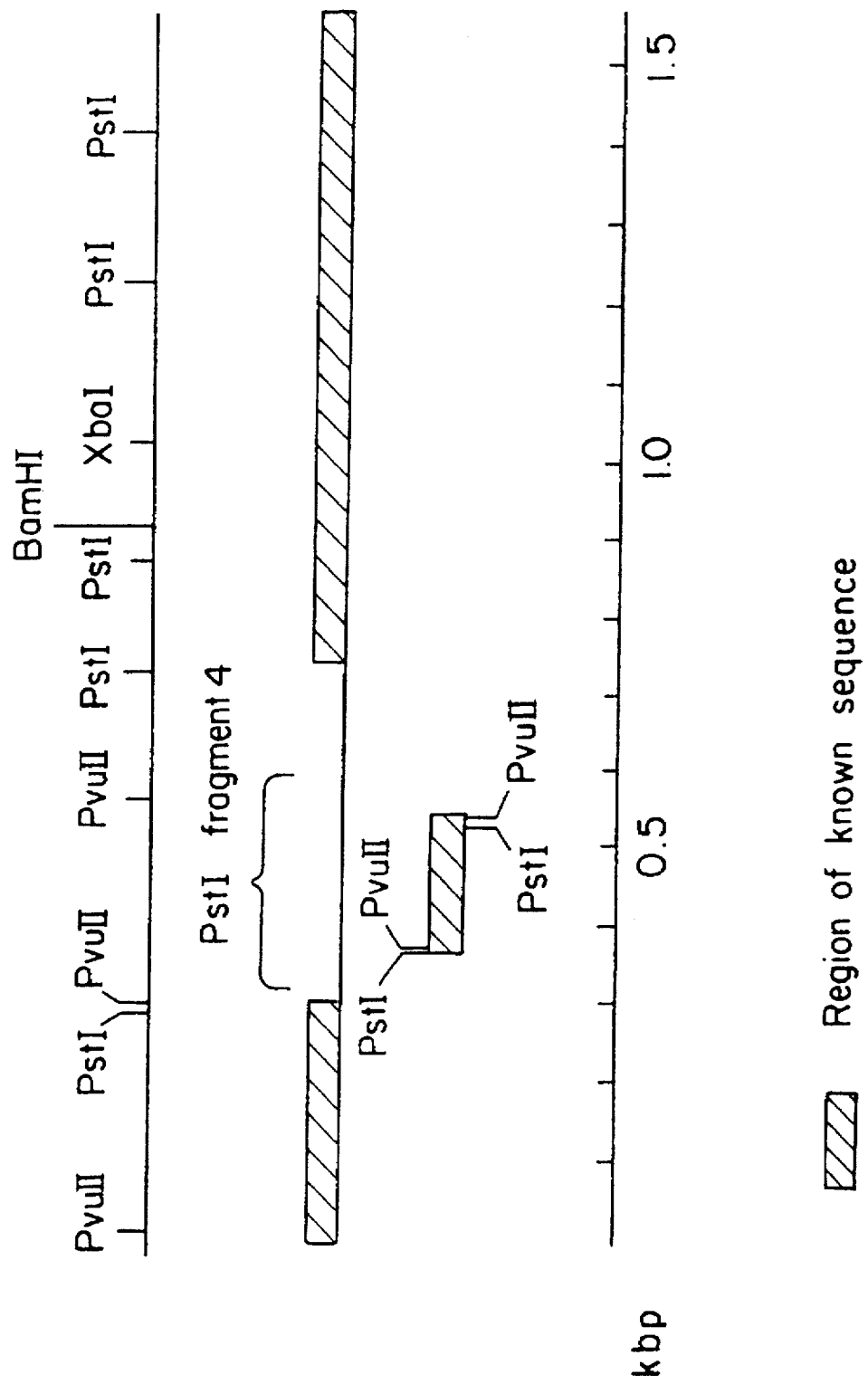
FIG. 6 shows a restriction map of the pMISS2 insert cDNA. Beneath the restriction map is a schematic showing the portions of the insert that have been sequenced.

The majority of the pMISS2 (encoding MiSP2) cDNA has been sequenced. The insert in pMISS2 is 1.6 kbp in length, of which 1344 nucleotides have been determined. The nucleotide sequence and translation of the completed portions of the DNA sequence are shown in FIG. 2A–2D. FIG. 6 shows a restriction map of the pMISS2 clone and indicates what portions of the cDNA insert have been sequenced. pMISS2 contains an open reading frame beginning at the 5' end of the insert that does not begin with a methionine. This result strongly suggests that the pMISS2 cDNA lacks nucleotides encoding the amino terminus of the MiSP2 protein. The pMISS2 cDNA, like the pMISS1 cDNA encodes a 5'-nonrepetitive region, a repetitive region and a 3'-nonrepetitive region. The 5'- and 3'-nonrepetitive regions of MiSP1 and MiSP2 are aligned in FIG. 4. In contrast to MiSP1, the unit repeat that characterizes the repetitive region in MiSP2 is cryptic. As no clear unit repeat is yet distinguishable, no consensus repeat unit is yet derived. However, it is clear from inspection of the repetitive portion of MiSP2 that it is distinguishable from the repetitive portion of MiSP1.

Another pair of clones, designated 11-1 and 11-2, respectively (collectively pMISS3), are independent isolates of the same cDNA and are found to encode a third minor ampullate silk polypeptide (MiSP3). 11-1 contains a 2 kbp insert; 11-2 contains a 1.5 kbp insert. Partial nucleotide sequences have been obtained from both of these clones to date. The nucleotide sequences and translations thereof are presented as FIGS. 3A–3C.

Three different types of N-bromosuccinimide (NBS) peptides from minor ampullate silk have been purified. The first type of peptide has the amino acid sequence GGQGGY (SEQ. ID. NO.:56). The second type of peptides have a sequence encompassed by the generic formula $(GA)_n$, where n=3.5, 4.5, or 8.5. The third type of peptides have the sequence $(G)_n$, where n=6 or 9. The pMISS1, pMISS 2, and pMISS3 clones all encode the GGQGGY (SEQ. ID. NO.:56) peptide and some variation of the $(GA)_n$ peptide. However, none of the isolated cDNAs, so far as they have been characterized to date, encode a $(G)_n$ peptide. Since pMISS1 has been completely sequenced, except for a small region of 42 nucleotides in a highly compressed region (high GC content) and does not contain the $(G)_n$ peptide, the minor ampullate silk must contain at least two proteins. Furthermore, while portions of the nonrepetitive regions of MiSP2 are identical to parts of the nonrepetitive regions MiSP1, the nonrepetitive regions of the two proteins are different. Also, the repetitive regions are different of MiSP1 and MiSP2 are distinguishable (see below). Although nonrepetitive portions have not yet been found in MiSP3, the repeats encoded by the 11-series isolates are distinguishable from the repeats of both MiSP1 and MiSP2 on two bases: (1) the spacing between Gln residues is only about one-half that seen in MiSP1 and MiSP2, and (2) Phe residues occasionally precede the GGQGGY (SEQ. ID. NO.:56) sequence whereas a Tyr always precedes the GGQGGY (SEQ. ID. NO.:56) sequence in MiSP1. Thus, the minor ampullate gland produces a silk comprised of at least three proteins.

EXAMPLE 2

Expression of a cDNA Encoding a Polypeptide Comprising the MaSp2 consensus sequence In order to demonstrate expression of an engineered spider silk protein, the consensus sequence from the MaSP2 protein (U.S. Ser. No. 07/684,819 was cloned into an *E. coli* expression vector. The consensus sequence was determined, using the considerations described above, from the alignment of the unit repeats of the MaSP2 protein. Table 2 shows the alignment of the unit repeats of the MaSP2 protein (SEQ. ID. NOS.:37–48).

TABLE 2

| Alignment of Unit Repeats of the MaSP2 Protein |
|---|
| GPGQQGPGGYGPGQQGP--SGPGSAAAAAAAAAA----GPGGYGPGQQGPGGY |
| GPGQQGPGRYGPGQQGP--SGPGSAAAAAA---------GSGQQGPGGY |
| GPRQQGPGGYGQGQQGP--SGPGSAAAASAAASAESGQQGPGGYGPGQQGPGGY |
| GPGQQGPGGYGPGQQGP--SGPGSAAAAAAAS--------GPGQQGPGGY |
| GPGQQGPGGYGPGQQGP--SGPGSAAAAAAAAS--------GPGQQGPGGY |
| GPGQQGPGGYGPGQQGL--SGPGSAAAAAAA------------------ |
| GPGQQGPGGYGPGQQGP--SGPGSAAAAAAAAA-------------GPGGY |
| GPGQQGPGGYGPGQQGP--SGAGSAAAAAAA----------GPGQQGLGGY |
| GPGQQGPGGYGPGQQGPGGYGPGSASAAAAAA------------------ |
| GPGQQGPGGYGPGQQGP--SGPGSASAAAAAAAA------------GPGGY |
| GPGQQGPGGYAPGQQGP--SGPGSASAAAAAAAA------------GPGGY |
| GPGQQGPGGYAPGQQGP--SGPGSAAAAAAASA-------------GPGGY |

The synthesis of the expression vector is described below and shown schematically in FIG. 7.

Two synthetic oligonucleotides were synthesized:

1) an 84 base oligonucleotide, named S2long (SEQ ID NO:50)
5'-TCTAGCCCGGGTGGCTATGGTCCTGGACAGCAAGGTCCTGGCGGTTACGGTCCTGGCCAACAGGGTCCCTCTGGTCACGGCAGT-3'
2) a 59 base oligonucleotide, named S2short (SEQ ID.NO:51)
5'-TCCGGACCTGCTGCGGCGGCTGCGGCAGCTGCACTGCCTGGACCAGAGGGACCCTGTTG-3'

These oligonucleotides were designed to hybridize to each other in a 27 base region of complementarity, on the 3' end of each respective oligonucleotide. When the rest of the bases were filled in by VENT™ polymerase (New England Biolabs) and the product digested with Xma I (recognition site-CCCGGG), a double-stranded segment of DNA resulted which encoded the basic repetitive unit of MaSP2 (SEQ. ID. NO.:52, in single letter amino acid code):

P G G Y G P G Q Q G P G G Y G P G Q Q G P S G P G-
S A A A A A A A A G

The DNA segment, with an Xma I cut on the 5' end (with respect to the coding strand) and the other end blunt but containing a Bsp EI site, was ligated into pBLUESCRIPT™ II (Stratagene) which had been double digested with Xma I and Eco RV and agarose gel purified, thus giving a directional cloning with the inserted segment in frame with the lac I gene of pBLUESCRIPT™ II. It is important to note for the strategy explained later that Xma I and Bsp E I have compatible, nonregenerable overlaps. That is, DNA cut with these enzymes can be ligated, but the ligation will not regenerate either site. The ligated DNA was subjected to Eco RI digestion to reduce background (the Xma I, Eco RV digest of the vector eliminated the unique Eco RI site of pBLUESCRIPT™ II) and used to transform competent SURE™ *E. coli* cells (Stratagene).

Twelve white colonies (indicating inserts were present in the plasmid) resulted which were screened by digesting plasmid DNA obtained from the colonies (SCREENMAX™, J. T. Baker) with BssHII to release the insert. The insert sizes were determined by agarose gel electrophoresis.

Four colonies contained inserts of the predicted size. Plasmid DNA was prepared from those colonies by SCREENMAX™ and subjected to sequencing. One colony harbored a plasmid (hereafter referred to as pS2U) containing an insert that was usable, although its structure was not exactly as designed. The ninth base of S2short was changed to a G, most likely a result of a synthesis error, although the difference may also have been a mistake incorporated by the polymerase or a mutation occurring during the cloning manipulations. In addition, the first base of S2short is missing (or the first base of the Eco RV site, it is impossible to determine which). This could be due to nonspecific nuclease activity in restriction enzymes used to perform the recombinant DNA manipulations. However, these changes are not critical, since the G appears in a wobble position in the coding sequence, and the alteration of the blunt end ligation site may even have provided some advantages, putting several codons for arginine directly after the MiSP2 sequence.

Figure 7:
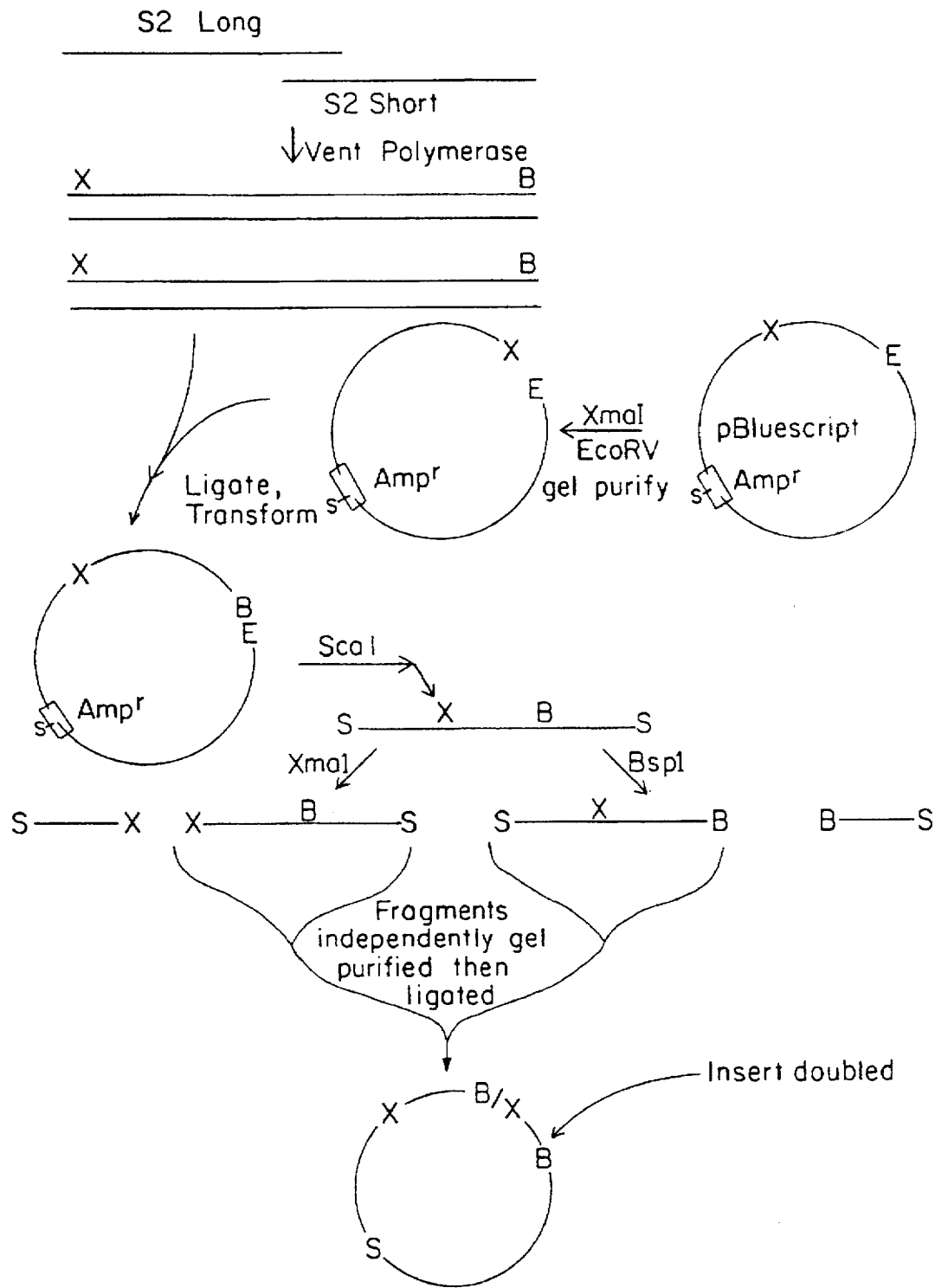
FIG. 7 shows a flow chart description of the synthesis of the pET19b-16 vector. Restriction sites are designated as: B, Bsp EI; E, Eco RV; S, Sca I; X, Xma I.

The insert was doubled, except for the additional arginine encoding codons, by manipulation of the restriction sites imbedded by design at the ends of the unit consensus sequence as well as a unique Sca I site in the ampicillin resistance gene of pBLUESCRIPT™ II (See FIG. 7). Plasmid from a miniprep is digested with Sca I, then divided into two aliquots. One aliquot is digested with Xma I and the other with Bsp E I. The digests are electrophoresed on 0.8% soft agarose, and the appropriate bands excised with a razor blade, and the DNA extracted using the standard procedure provided with β-agarase (New England Biolabs). The Sca I-Xma I segment containing one copy of the unit is then ligated to the Sca I-Bsp EI segment also containing one copy of the unit, thus effectively doubling the insert size while keeping both units in frame and regenerating the ampicillin resistance. This strategy can be repeated to derive any number of repeats of the unit desired (until secondary structure or insert size interferes). Thus an engineered vector encoding a polypeptide comprising 16 repeats of the MaSP2 consensus sequence was constructed in pBLUESCRIPT™ II.

The insert encoding 16 repeating units of the MaSP2 consensus sequence was placed in pET19b by cutting the HincII site of pBLUESCRIPT™ (creating a blunt end) then ligating a Bam H1 linker of the appropriate size to that end. The fragment was then subjected to Bam H1 cleavage, which cut at both ends, due to the presence of a Bam H1 site in pBLUESCRIPT™ a few bases 5' of the insert. This 5' Bam H1 site was engineered to be in frame with the Bam H1 insertion site of the pET system of vectors (Novagen). As noted below, the pET vector system allows affinity purification of expressed proteins using affinity recognition of a polyhistidine leader sequence attached to the desired protein. The insert was agarose gel purified, ligated into Bam H1-cut, phosphatased pET19b and the result used to transform competent SURE™ E. coli (Stratagene). The resultant colonies were screened and the orientation of the inserts determined by restriction digest. Clones with properly oriented inserts were then used for expression experiments.

BL31 DE3 E. coli (Novagen) were transformed with a plasmid having the insert in the desired orientation (pET19b-16) and plated on LB agarose plates containing chloramphenicol and carbenicillin. Antibiotic resistant colonies were picked an grown in LB medium containing chloramphenicol and carbenicillin to an $OD_{600}$ of about 0.8. One mL of the resulting inoculum was saved as a freezer stock. Inoculum cultures should be grown to $OD_{600}$ of 0.8 or less, in order to maintain antibiotic selection pressure.

Five mL of the inoculum was used to inoculate 50 mL of LB containing the antibiotics. When the $OD_{600}$ reached 0.8, the cells were collected by centrifugation and resuspended in 50 mL of fresh medium. The resuspended culture was diluted into 500 mL of LB containing the antibiotics and culture was continued until the $OD_{600}$ reached 0.8. IPTG was added to a concentration of 0.8 mM to initiate expression of the synthetic spider silk gene.

After four hours, the cells were collected by centrifugation and resuspended in a lysis buffer modified from the method of Sambrook et al. (50 nM Tris-Cl (pH 8.0), 10 mM $MgCl_2$, 100 mM NaCl), and lysed with lysozyme in the presence of pMSF according to Sambrook et al. [J. Sambrook et al., *Molecular Cloning: A Laboratory Manual*, 2nd ed., pp. 17.23–17.44, c. 1989 by Cold Spring Harbor Laboratory press, Cold Spring Harbor, N.Y.].

The MaSP2 consensus polypeptide was purified from the lysate by affinity purification using a $Ni^{2+}$ column, as described by the technical manual provided by the manufacturer (Novagen). The divalent metal complexes the polyhistidine leader sequence encoded by the pET vector. A single step affinity purification provided the desired fusion protein at 95% purity.

Figure 8A:
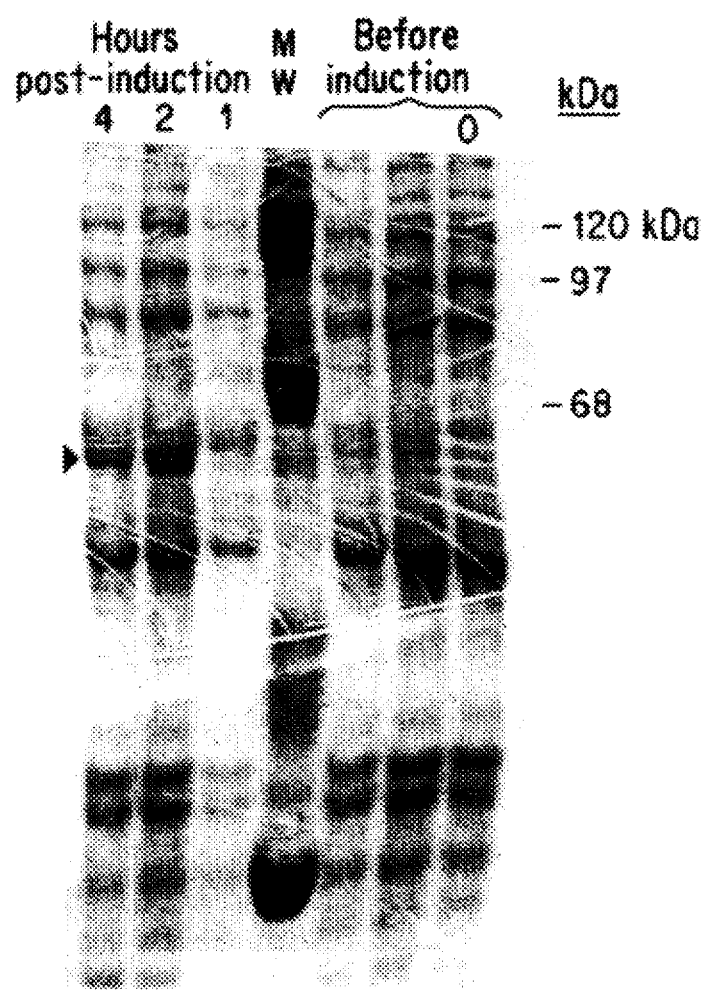
FIG. 8A–8B shows analysis of the purification of a synthetic spider silk protein expressed from the pET19b-16 vector. 8A shows analysis of the crude lysate at 1, 2 and 4 hours post-induction. 8B shows analysis of the protein purified by $Ni^{2+}$ affinity purification.
Figure 8B:
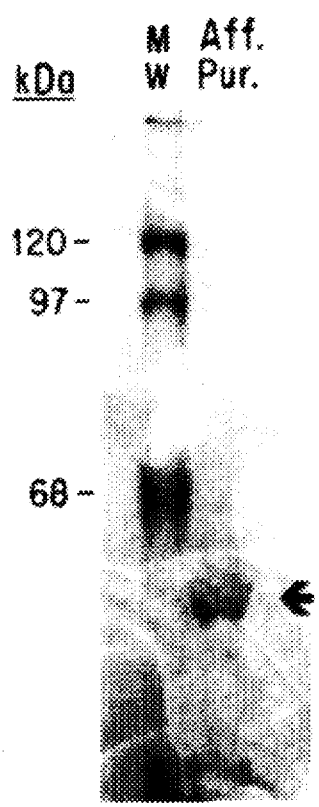

For cleavage of the polyhistidine leader peptide, the eluant from the affinity column was dialysed against distilled water for 24 hours to remove salts. The solution was made to 25 mM in ammonium bicarbonate and TPCK-treated trypsin was added to 1/20 the amount of the protein content of the eluate by weight. The digestion reaction was incubated at 37° C. for 4 hours. An additional aliquot of trypsin was added and the incubation was continued for an additional 4 hours. The leader peptide fragment was separated from the synthetic spider silk polypeptide by gel filtration chromatography on SEPHADEX™ G-50. FIG. 8 shows the results obtained using the above-described system. Approximately 10 mg of the MiSP2 consensus polypeptide are obtained from a 500 mL culture. The molecular weight of 58 kDa is the expected molecular weight for the polypeptide having a sequence of 16 repeats of the MiSP2 consensus sequence.

EXAMPLE 3

A Generalized Method for Preparing Vectors for Expression of Spider Silk Protein Consensus Polypeptides Following is a general method for generating artificial genes for any repetitive protein that contains polyalanine stretches. The method can thus be applied to express a protein comprising the consensus polypeptide of any of the major or minor ampullate spidroin proteins described herein.

The method employs two particular restriction enzymes, Sfi I and AlwN I (recognition sites shown below):

Sfi I: GGCCNNNN/NGGCC (SEQ. ID. NO.:53) AlwN I: CAGNNN/CTG

An oligomer is designed such that a Bam HI site is in frame with and immediately precedes an Sfi I site. The Bam H I site will also be in frame with the pET system of vectors which are used for expression. However, the manipulations which are needed to produce multiple copies of the artificial unit will not involve this site, since it is 5' to the Sfi I site. Sfi I and AlwN I are used as the primary enzymes for manipulations for unit multiplication because the recognition sequences of both of these enzymes can (1) code for polyalanine stretches (see below) and (2) can form a pair of compatible, nonregenerable sites.

Ala Ala Ala Ala (SEQ. ID. NO.: 55)
Sfi I: G/GCC/GCA/GCG/GCC (SEQ. ID.: 54)

Ala Ala Ala
AlwN I: GCA/ GCA/GCT

Two oligonucleotides are designed that will reverse complement each other on their 3' ends, allowing hybridization. The first contains the Bam HI site, followed (in frame) by the Sfi I site representing the polyalanine region of MiSP1, followed by DNA encoding approximately two-thirds of the repetitive portion of MiSP1. The second oligonucleotide will be the anti-coding strand of MiSP1, starting with an AlwN I site and encoding approximately two-thirds of the repetitive region.

The simple diagram below shows the intended overlap of the the oligonucleotides and the placement of the restriction enzymes sites.

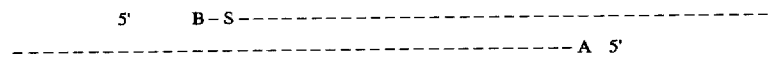

After hybridization, the overhanging ends are filled with VENT™ polymerase. The resultant double-stranded product is digested with Bam H I and, after agarose gel purification, cloned into a Bam H I cut, Eco R V cut pBLUESCRIPT™ II vector. This ligation mixture is digested with Eco R I (to reduce background) and used to transform competent SURE™ E. coli cells. Plasmid DNA is prepared from resulting colonies and screened first for insert size, then sequenced to determine if the insert is properly integrated.

To double the insert to appropriate size, double digests with Sca I (found in the Amp$^r$ gene of BLUESCRIPT™TM) and either Sfi I-or AlwN I are performed and the resultant fragments gel purified. The 5' Sca I-Sfi I-AlwN I 3' fragment of the Sca I + AlwN I digest is ligated to the 5' Sfi I-AlwN I-Sca I 3' fragment from the Sca I + Sfi I digest. This will regenerate a functional pBLUESCRIPT™ II which will include a doubled artificial gene. Since Sfi I and AlwN I ends are compatible they will ligate, but the resulting splice site will not regenerate a recognition site for either enzyme. This allows the doubling to be extended to 4-, 8-, 16-, and higher multimers of the original insert.

The final vector+ multimer can then be cut with Hinc II, ligated with Bam H I linkers of an appropriate length, cut with Bam H I to liberate the insert, and cloned directly into the pET system of vectors for expression.

EXAMPLE 4
Optimization of Expression of DNA Encoding Spider Silk Proteins

In order to increase the yield of spider silk proteins expressed from cloned DNA in bacteria, the above-described culture methods can be modified. In particular, due to the large proportion of glycine, alanine, glutamine and proline in the proteins, supplementation of the culture medium used to grow cells for expression with these amino acids is expected to allow increased yield of the spider silk protein. Also, the culture density can be increased by use of high-density fermentation methods standard in the art [See, e.g. Reisenburg et al., Applied Microbiology and Biotechnology 34:77 (1990); Alberghina et al., Applied Microbiology and Biotechnology 34:82 (1990)]. For instance, increasing the $OD_{600}$ at which expression is initiated from 0.8 to 20 would be expected to produce a concomittant increase in yield from 20 mg/L to 480 mg/L.

The vector used to support replication of the cloned DNA and to drive its expression can also be changed. The basic pET system described above is available from the supplier (Novagen) in many variations. One characteristic which makes the pET system advantageous is that expression of inserts in the pET vectors is very tightly regulated. Very little of the cloned DNA is expressed until transcription of the insert DNA is induced. When transcription is induced, additional elements of the pET vector inhibit production of host cell proteins, thereby putting most of the protein synthetic resources of the cell to work to make protein encoded by the insert DNA.

However, the use of chloramphenicol and carbenicillin resistance to provide selection pressure is disadvantageous for high-level expression of proteins. Accordingly, use of a different antibiotic selection, e.g. kanamycin resistance, is expected to provide increased yields of protein by expression of DNA cloned in pET vectors.

Another advantage of the system used in the present case is that the polyhistidine leader peptide provides an affinity purification method that can be used even in the presence of chaotropic agents. This would allow purification of spider silk proteins fused to such a polyhistidine sequence which might be made in "inclusion bodies", aggregates of insoluble protein, that require harsh solubilization procedures prior to purification.

The host cell strain used for expression can also be optimized. Cells having a high level of tRNA for Ala, Gln, Gly and pro codons could be made and used for expression of spider silk proteins. Also, the cellular protease complement of the cells can be manipulated to minimize degradation of the expressed protein.

It is considered that the spider silk proteins of the present invention can be expressed in appropriately engineered insect cells, using commonly available baculovirus vectors.

EXAMPLE 5
Preparation of Fibers From Spider Silk Proteins

As noted above, the spider silk proteins can be viewed as derivatized polyamides. Accordingly, the methods for producing fiber from soluble spider silk proteins is similar to that used to produce typical polyamide fibers, e.g. nylons, and the like.

O'Brien et al. [supra] describe fiber production from adenovirus fiber proteins. In a typical fiber production, the spider silk proteins are solubilized in a strongly polar solvent. The protein solution is typically greater than 5% in protein concentration. The solution is preferably between 8 and 20% in protein.

Fibers are preferably spun from solutions demonstrating properties indicating a liquid crystal phase. The concentration at which the phase transition will occur is different for particular polypeptide compositions. However, the phase transition can be monitored by observing the clarity and birefringence of the solution. Onset of the a liquid crystal phase is detected by a translucent appearance of the solution and the observation of birefringence when the solution is viewed through crossed polarizing filters.

The solvent used to dissolve the spider silk protein is preferably highly polar. Such solvents are exemplified by di- and tri- haloacetic acids, haloalcohols (e.g.

hexafluoroisopropanol). In some instances, co-solvents such as acetone are useful. Also, solutions of chaotropic agents, such as lithium thiocyanate, guanadine thiocyanate or urea can be used.

In one fiber-forming technique, fibers are first extruded from the protein solution through an orifice into methanol, until a length sufficient to be picked up by a mechanical means is produced. Then the fiber is pulled by such mechanical means through the methanol solution, collected and dried. The methods for drawing fibers are considered well-known in the art. Fibers made from the 58 kDa synthetic MaSp consensus polypeptide, described in Example 2, for instance, can be drawn by methods similar to those used for drawing low molecular weight nylons.

The invention being thus described, various modifications of the materials and methods disclosed herein will be apparent to one of skill in the art. Such modifications are to be considered encompassed by the scope of the invention described by the claims below. Articles of the scientific and patent literature cited herein are incorporated by reference in their entirety by such citation.

We claim:

1. A purified polypeptide having an amino acid sequence comprising repeats of the unit amino acid sequence of SEQ ID NO.:32.

2. A purified polypeptide having the amino acid sequence shown in SEQ ID NO.:2.

3. A purified polypeptide comprising one or more repeats of a unit amino acid repeat sequence selected from the group consisting of SEQ ID NO.:19, SEQ ID NO.:20, SEQ ID NO.:21, SEQ ID NO.:22, SEQ ID NO.:23, residues 1–34 of SEQ ID NO.:23, SEQ ID NO.:24, SEQ ID NO.:25, SEQ ID NO.:26, SEQ ID NO.:27, SEQ ID NO.:28, SEQ ID NO.:29, SEQ ID NO.:30 and SEQ ID NO.:31.

4. A purified polypeptide according to claim 3, wherein all repeats are of the same unit amino acid repeat sequence.

5. A purified polypeptide according to claim 3 further comprising an amino terminal polypeptide having the amino acid sequence of residues 2–155 of SEQ ID NO.:2.

6. A purified polypeptide according to claim 3 further comprising an amino terminal polypeptide having the amino acid sequence of residues 1–88 of SEQ ID NO.:4.

7. A purified polypeptide according to claim 3 further comprising a carboxy terminal polypeptide having the amino acid sequence of SEQ ID NO.:17.

8. A purified polypeptide according to claim 3 further comprising a carboxy terminal polypeptide having the amino acid sequence of residues 137 to 251 of SEQ ID NO.:8.

9. A purified polypeptide according to claim 5 further comprising a carboxy terminal polypeptide having the amino acid sequence of SEQ ID NO.:17.

10. A purified polypeptide according to claim 5 further comprising a carboxy terminal polypeptide having the amino acid sequence of residues 137 to 251 of SEQ ID NO.:8.

11. A fiber consisting essentially of polypeptides according to any one of claims 1 through 10.

12. A fiber consisting essentially of mixed polypeptides selected from the group consisting of polypeptides according to claim 1 and polypeptides according to claim 2, polypeptides according to claim 1 and polypeptides according to claim 3, polypeptides according to claim 1 and polypeptides according to claim 5, polypeptides according to claim 1 and polypeptides according to claim 6, polypeptides according to claim 2 and polypeptides according to claim 3, polypeptides according to claim 2 and polypeptides according to claim 5, polypeptides according to claim 2 and polypeptides according to claim 6, polypeptides according to claim 3 and polypeptides according to claim 5, polypeptides according to claim 3 and polypeptides according to claim 6, polypeptides according to claim 5 and polypeptides according to claim 6.

13. A fiber consisting essentially of polypeptides according to claim 5 and polypeptides according to claim 6.

14. A purified polypeptide comprising repeats of an amino acid sequence having the generic formula $$(GR)(GA)_l(A)_m(GGX)_n(GA)_l(A)_m$$

where X is tyrosine, glutamine or alanine and
where l=1 to 6, m=0 to 4 and n=1 to 4.

15. A purified polypeptide comprising direct repeats of an amino acid sequence having the generic formula:

$$(GGX)_n(GA)_m(A)_l$$

where X is tyrosine, glutamine or alanine and
where l=1 to 6, m=0 to 4 and n=1 to 4.

16. A polypeptide according to any one of claims 1–10, and 14 and 15, wherein said polypeptide has a molecular weight ranging from 16,000 to 300,000 daltons.

* * * * *